(12) United States Patent  
Alexander

(10) Patent No.: US 10,751,064 B2  
(45) Date of Patent: Aug. 25, 2020

(54) SYSTEMS AND METHODS FOR DELIVERING AN IMPLANTABLE DEVICE

(71) Applicant: Edwards Lifesciences Corporation, Irvine, CA (US)

(72) Inventor: Miles D. Alexander, Fremont, CA (US)

(73) Assignee: Edwards Lifescience Corporation, Irvine, CA (US)

( * ) Notice: Subject to any disclaimer, the term of this patent is extended or adjusted under 35 U.S.C. 154(b) by 223 days.

(21) Appl. No.: 15/559,680

(22) PCT Filed: Mar. 17, 2016

(86) PCT No.: PCT/US2016/022863
§ 371 (c)(1),
(2) Date: Sep. 19, 2017

(87) PCT Pub. No.: WO2016/153918
PCT Pub. Date: Sep. 29, 2016

(65) Prior Publication Data
US 2018/0049746 A1    Feb. 22, 2018

Related U.S. Application Data

(60) Provisional application No. 62/136,248, filed on Mar. 20, 2015.

(51) Int. Cl.
*A61B 17/12*    (2006.01)
*A61B 17/00*    (2006.01)

(52) U.S. Cl.
CPC .. *A61B 17/12122* (2013.01); *A61B 17/12172* (2013.01); *A61B 17/12177* (2013.01); *A61B 2017/0053* (2013.01); *A61B 2017/12054* (2013.01); *A61B 2217/007* (2013.01)

(58) Field of Classification Search
CPC .. A61B 2017/00623; A61B 2017/1205; A61B 2217/007; A61F 2/95; A61F 2002/011
See application file for complete search history.

(56) References Cited

U.S. PATENT DOCUMENTS

2014/0296624 A1* 10/2014 Kermode ......... A61B 17/12122
600/37

* cited by examiner

*Primary Examiner* — Melanie R Tyson
(74) *Attorney, Agent, or Firm* — Snell & Wilmer L.L.P.; Hans P. Smith

(57) ABSTRACT

A delivery system for delivering an implantable device can include a delivery catheter, a sleeve, and a guide catheter. The delivery catheter can have a tubular body having a proximal end and a distal end, such that the distal end of the delivery catheter is configured to couple to the implantable device. The sleeve can define a lumen configured to receive the delivery catheter and the implantable device coupled thereto. A first fluid delivery port can be positioned on the delivery catheter or the sleeve. A mechanical seal can be coupled to the sleeve and configured to form a liquid-tight seal with the delivery catheter. A guide catheter can have a tubular body having a proximal end, a distal end, and a second fluid delivery port positioned thereon, wherein the proximal end of the guide catheter is configured to be connected to a distal end of the sleeve.

31 Claims, 18 Drawing Sheets

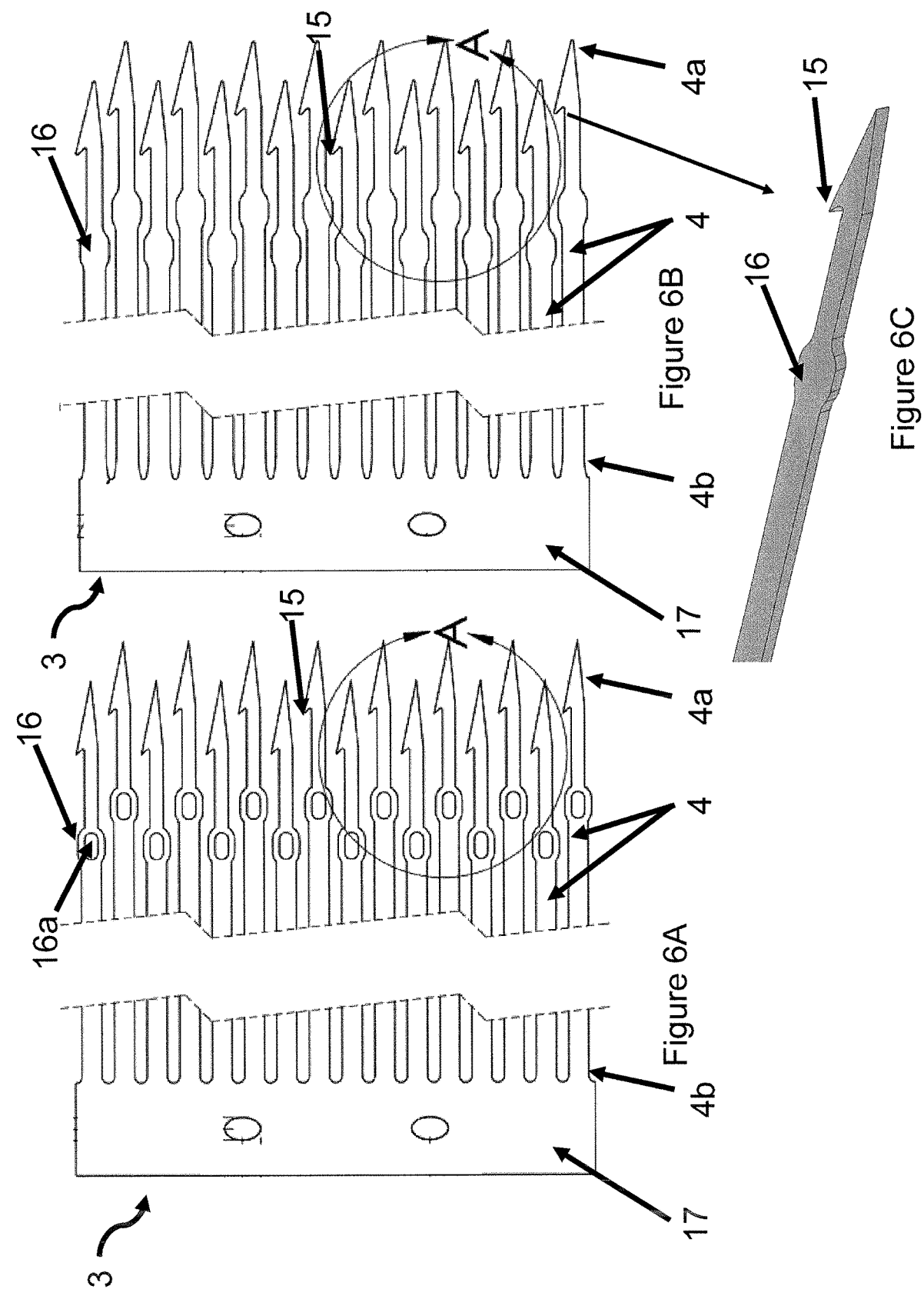

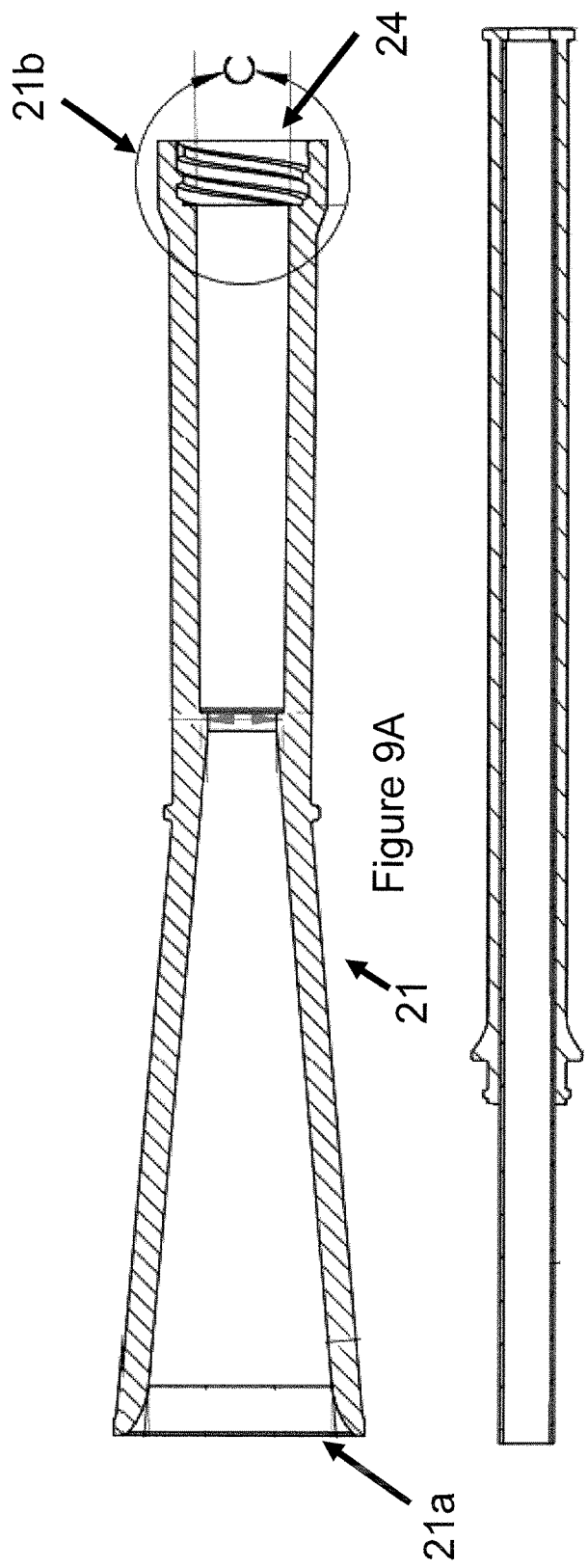
Figure 9A
Figure 9B
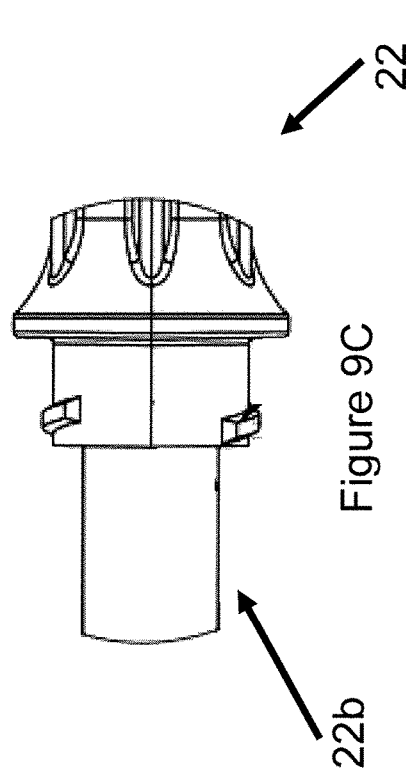
Figure 9C

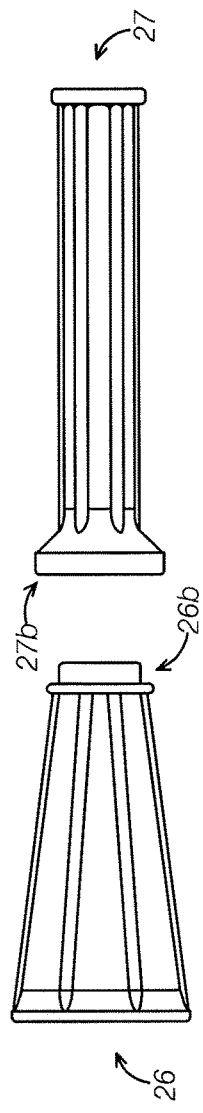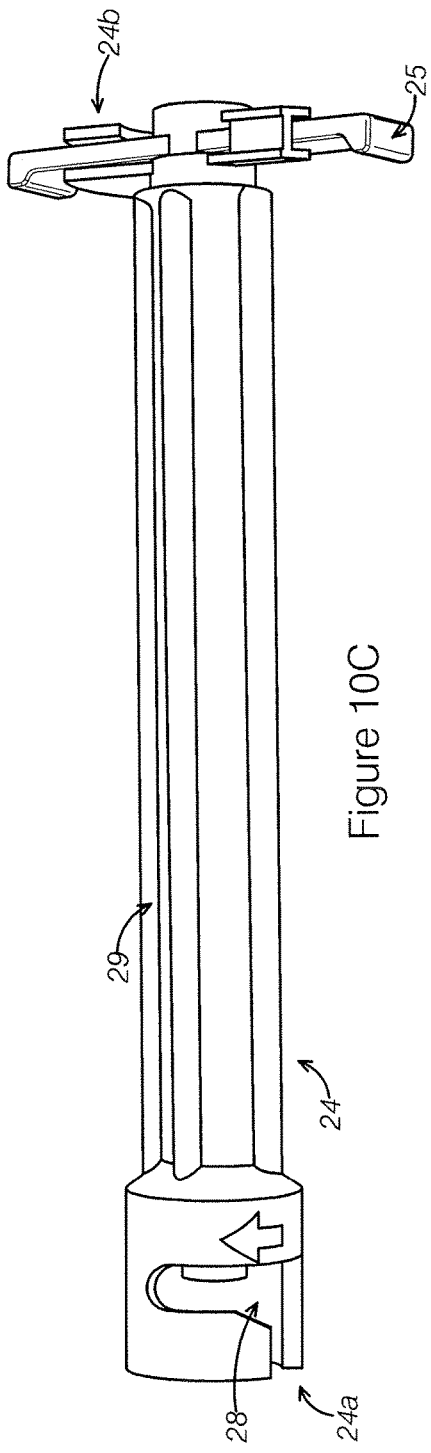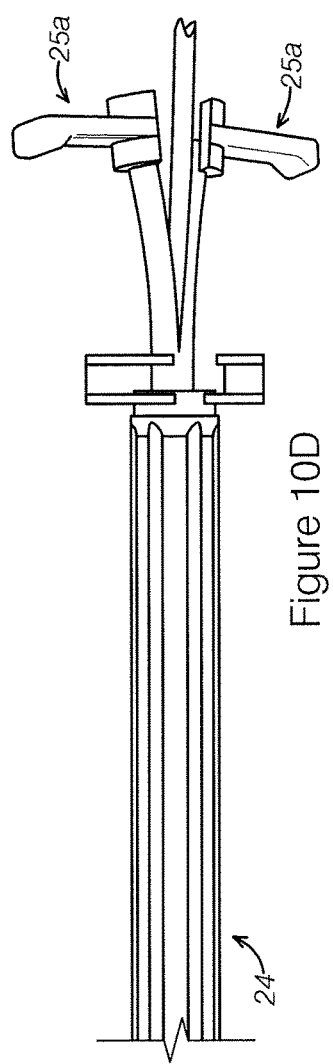
Figure 10A  Figure 10B  Figure 10C  Figure 10D dimensions than those of a healthy heart. Elastic recoil forces are important in early diastole because they allow rapid and enhanced early filling by assisting the expansion of the left ventricle.

SYSTEMS AND METHODS FOR DELIVERING AN IMPLANTABLE DEVICE

CROSS REFERENCE TO RELATED APPLICATIONS

This application claims priority to U.S. Provisional Application No. 62/136,248, filed Mar. 20, 2015, and titled "SYSTEMS AND METHODS FOR DELIVERING AN IMPLANTABLE DEVICE", which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

This invention relates to the field of ventricular devices useful for treating cardiac dysfunction.

BACKGROUND

Congestive heart failure (CHF) is a chronic medical condition in which the heart progressively enlarges. The enlarged heart cannot deliver sufficient oxygenated and nutrient rich blood to the body's cells. CHF is commonly associated with left ventricular dysfunction and/or diastolic dysfunction. Left ventricular dysfunction results from impaired emptying of the left ventricular heart chamber. In contrast, diastolic dysfunction refers to alterations in left ventricular properties that adversely affect ventricular filling and diastolic pressure.

A key aspect of normal diastolic filling is the contribution of left ventricular elastic recoil forces to left ventricular filling. Elastic recoil is the ability of the stretched heart to return to its resting position. For example, in a healthy heart, the end-diastolic dimension of the left ventricle may range from 36-56 mm (relaxed) and the end-systolic dimension of the left ventricle may range from 20-40 mm (contracted). A left ventricle in heart failure would typically have larger dimensions than those of a healthy heart. Elastic recoil forces are important in early diastole because they allow rapid and enhanced early filling by assisting the expansion of the left ventricle.

In the case of heart enlargement and/or a decrease in myocardial function, elastic recoil forces may be reduced or absent, thus ceasing to assist early ventricular filling and leading to an increase of the ventricular filling pressure. For example, a patient experiencing CHF typically has an ejection fraction of 40% or less.

Thus, there is a need for a new and useful system, device, and method for treating cardiac dysfunction. This invention provides such a new and useful system, device, and method.

SUMMARY

The present disclosure is directed to systems and methods for implantable device delivery. One aspect of the disclosure is directed to a delivery system for an implantable device. In some embodiments, a delivery system for an implantable device includes a delivery catheter including a tubular body having a proximal end and a distal end; a sleeve defining a lumen configured to receive the delivery catheter and the implantable device coupled thereto; a first fluid delivery port positioned on the delivery catheter or the sleeve; a mechanical seal coupled to the sleeve and configured to form a liquid-tight seal with the delivery catheter; and a guide catheter comprising a tubular body having a proximal end, a distal end, and a second fluid delivery port positioned thereon.

In some embodiments, the distal end of the delivery catheter is configured to couple to the implantable device. In some embodiments, the proximal end of the guide catheter is configured to be connected to a distal end of the sleeve. In some embodiments, the guide catheter includes a hemostatic valve positioned at the proximal end of the guide catheter.

In some embodiments, a first pressure in the guide catheter is greater than a second pressure in a ventricle when fluid is delivered through the guide catheter. In some embodiments, the system includes a pressurized fluid reservoir. In one embodiment, the pressurized fluid reservoir is configured to be in fluid communication with the delivery catheter. In some embodiments, the system includes a pump. In one embodiment, the pump is configured to deliver fluid through the delivery catheter.

In some embodiments, the mechanical seal is a gasket.

In some embodiments, the implantable device is a ventricular partitioning device. In one embodiment, the implantable device includes a support frame including a plurality of radially expandable struts and a membrane coupled to the support frame. In one embodiment, the implantable device includes a foot for contacting a first interior wall portion of the ventricle.

In some embodiments, the first pressure in the guide catheter is about 200-600 mm Hg. In some embodiments, the second pressure in the ventricle is about 50-300 mm Hg.

In some embodiments, the fluid is delivered at a positive pressure into the first and/or second fluid delivery ports.

In some embodiments, the system includes a funnel. In one embodiment, the funnel includes a flared first end and a second end. In one embodiment, the flared first end is configured for receiving and collapsing the expandable device. In one embodiment, the second end of the funnel is coupleable to the sleeve.

One aspect of the disclosure is directed to methods of preparing a ventricular partitioning device for implantation. In some embodiments, a method of preparing a ventricular partitioning device for implantation using a delivery system includes coupling the ventricular partitioning device to a delivery catheter; loading the ventricular partitioning device and a portion of the delivery catheter into a sleeve and creating a liquid-tight seal between a portion of the sleeve and the delivery catheter; coupling a distal end of the sleeve to a guide catheter; and delivering fluid through the first fluid delivery port and/or the second fluid delivery port.

In some embodiments, the delivery catheter or the sleeve includes a first fluid delivery port positioned thereon. In some embodiments, the guide catheter includes a second fluid delivery port positioned thereon.

In some embodiments, the step of delivering the fluid creates a first pressure in the guide catheter that is greater than a second pressure in a ventricle In some embodiments, the method includes transferring the ventricular partitioning device from the sleeve to the guide catheter. In some embodiments, the method includes delivering the ventricular partitioning device from the guide catheter into the ventricle. In some embodiments, the method includes uncoupling the delivery catheter from the ventricular partitioning device.

In some embodiments, the method includes loading the ventricular partitioning device into a funnel device. In one embodiment, the funnel device includes a flared first end and a second end. In one embodiment, the flared first end is configured for receiving and collapsing the expandable device.

In some embodiments, the sleeve is removably coupled to the second end of the funnel device. In one embodiment, the sleeve is configured for receiving the expandable device from the funnel device.

In some embodiments, the delivering fluid step includes delivering the fluid at a positive pressure. In some embodiments, the method includes maintaining the positive pressure in the guide catheter during delivery of the ventricular partitioning device into the ventricle.

In some embodiments, the first pressure in the guide catheter is about 200-600 mm Hg. In some embodiments, the second pressure in the ventricle is about 50-300 mm Hg.

In some embodiments, the method includes aspirating gas from the delivery system through the second fluid delivery port while fluid is delivered through the first fluid delivery port.

In some embodiments, the method includes removing bubbles from the delivery system using the first and/or second fluid delivery ports.

In some embodiments, the method includes allowing blood to exit the delivery system through the second fluid delivery port disposed on the guide catheter as the ventricular partitioning device is advanced from the sleeve into the guide catheter.

In some embodiments, delivering fluid through the first fluid delivery port and/or the second fluid delivery port includes delivering fluid through the first fluid delivery port into the guide catheter as the ventricular partitioning device is advanced through the guide catheter.

In some embodiments, the fluid is substantially maintained in the delivery system by the liquid-tight seal.

In some embodiments, the method includes sealing the second fluid delivery port disposed on the guide catheter at a time after the ventricular partitioning device has advanced distally beyond the second fluid delivery port.

In some embodiments, the delivering fluid step includes delivering the fluid using a pump at a flow rate between about 0.5 to 5 ml/second.

BRIEF DESCRIPTION OF THE DRAWINGS

FIGS. 6A-6C illustrate two embodiments of the struts of a ventricular partitioning device;

FIGS. 9A-9C illustrate a cross-sectional view of one embodiment of an implant loading system for a ventricular partitioning device;

FIGS. 10A-10D illustrates an alternative embodiment of an implant loading system for a ventricular partitioning device;

FIG. 5A illustrates one embodiment of guide catheter comprising two hemostatic valves;

DETAILED DESCRIPTION

Disclosed herein are systems and devices for treating cardiac dysfunction. In some instances, cardiac dysfunction may include diastolic dysfunction, mitral valve regurgitation, and/or heart failure.

In general, the systems and devices described herein may be used to treat a patient's heart suffering from heart failure. The systems and devices may be used to treat a patient's heart experiencing diastolic dysfunction or a condition exhibiting characteristics of diastolic dysfunction, and may involve implanting, within a ventricle of the heart, a device that partitions the ventricle into functional and nonfunctional portions. In some embodiments, the device may deform during systole and recoil during diastole to supplement the natural elastic recoil action of the ventricle. In some embodiments, the device may reduce the end-diastolic volume, end-diastolic pressure, and/or increase the ejection fraction.

Diastole represents the period of time in the heart cycle in which the ventricles are relaxed and not contracting. Throughout most of diastole, blood is passively flowing from the right and left atria into the right and left ventricles, respectively. As the ventricles begin to contract, the pressure in the ventricles exceeds that of the atria, and the mitral valve closes, ending diastole. At this time, the ventricular pressure and volume are referred to as end-diastolic pressure and end-diastolic volume, respectively.

Reduced ventricular compliance, for example due to an increased stiffness in the ventricular heart wall, may result in increased end-diastolic pressure and decreased end-diastolic volume. Diastolic dysfunction may also result from changes in left ventricle relaxation during diastole. For example, inotropic stimulation, fast heart rates, non-uniform heart activation, and altered timing of forces that oppose ventricular ejection may contribute to altered left ventricle relaxation.

Devices

Figure 1:
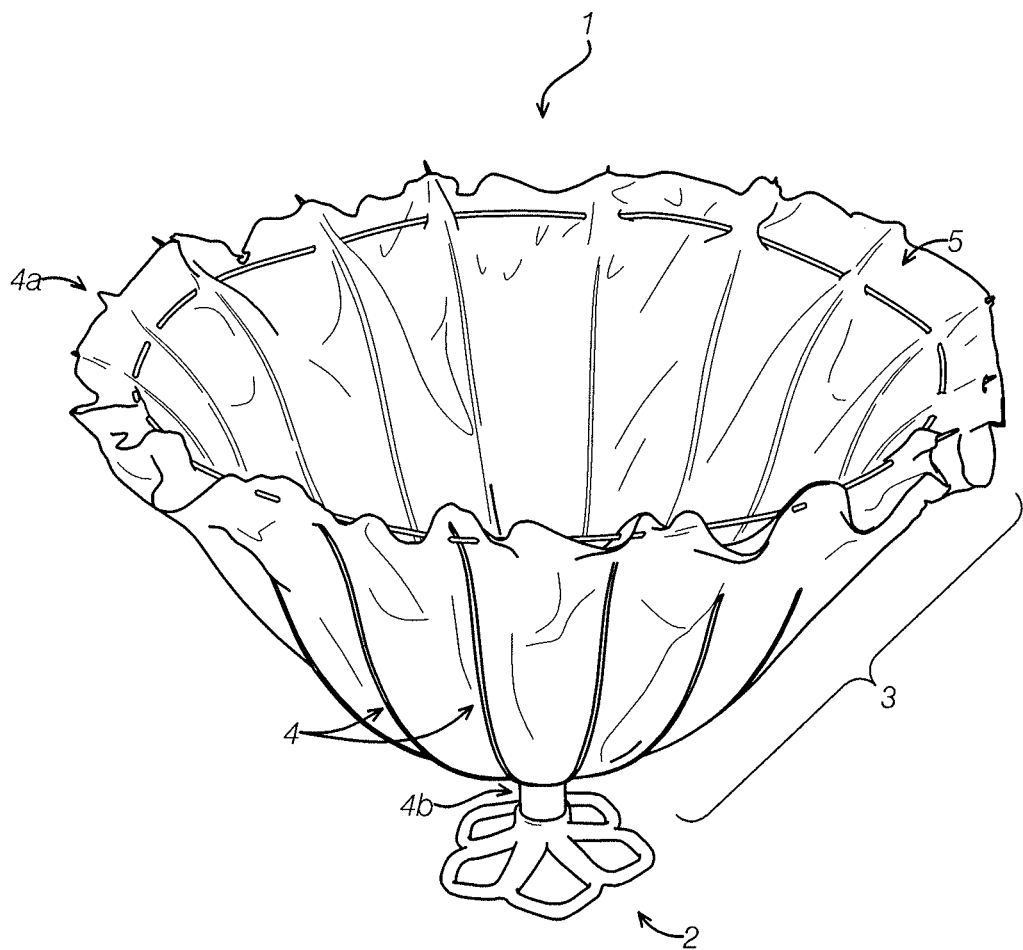
FIG. 1 illustrates one embodiment of a ventricular partitioning device.

FIG. 1 illustrates an expandable or implantable device, which may also be referred to as a ventricular partitioning device, 1 to treat cardiac dysfunction. In some embodiments, cardiac dysfunction may include diastolic dysfunction, mitral valve regurgitation, heart failure, and/or any other type of malady of the heart. The device may be delivered to the ventricle of a patient to treat cardiac dysfunction. In some embodiments, as shown in FIG. 1, a device for treating cardiac dysfunction may include a foot 2 for contacting a first interior wall portion of a heart. Further, in some embodiments, a device for treating cardiac dysfunction may include a support frame 3 including a plurality of radially expandable struts 4 and a membrane 5 coupled to the support frame 3. Each of the radially expandable struts 4 has a first free end 4a and a second end 4b coupled to the foot 2.

FIGS. 2A-2D and 3A-3C illustrate two embodiments of a foot 2 coupled to a stem 6 of an expandable device. The foot 2 of a ventricular partitioning device may contact an interior wall portion of a heart of a patient experiencing cardiac dysfunction. An interior wall portion of a heart may include an apex of a ventricle. In some embodiments, the foot 2 may contact the apex of the ventricle so that the entire device is underneath the papillary muscle located in the ventricle, such that the ventricular partitioning device does not interfere with the heart valve in the apex of the ventricle. In some embodiments, the foot 2 may contact the apex of the ventricle atraumatically such that the apex of the ventricle does not incur damage, trauma, and/or significant injury.

The foot 2 of the device, as shown in FIGS. 2A-3C, is supportive such that it does not collapse upon itself once implanted. However, the foot 2 may also be flexible, such that the device does not create focal pressure points (e.g., "hot spots") in the ventricle. To balance these properties of the ventricular partitioning device, the foot 2 of the ventricular partitioning device may include a thermoplastic elastomer. In some embodiments, the foot 2 may include thermoplastic silicone polyether polyurethane (TPU), such as DSM.

In some embodiments, as shown in FIGS. 2A-3C, the foot 2 may include a different material and/or durometer than the stem. In some embodiments, the foot 2 may include, Pursil TSPU, or any other thermoplastic material, such that the durometer is 70A to 90A and the flexural modulus or bending modulus is 15 MPa to 45 MPa. In one embodiment, the foot includes a durometer of 78A to 84A and a flexural modulus or bending modulus of 20 MPa to 40 MPa. In some embodiments, the stem 6 may include elasthane TPU, or any other thermoplastic material, such that the durometer is 45D to 75D and the flexural modulus or bending modulus is 100 MPa to 400 MPa. In one embodiment, the stem includes a durometer of 50D to 70D and a flexural modulus or bending modulus of 145 MPa to 390 MPa.

In some embodiments, the foot 2 of the ventricular partitioning device may include a radiopaque filler material to aid in visualization of the implant during and/or after implantation of the ventricular partitioning device in the heart of a patient. In some embodiments, the foot 2 may include 20% radiopaque filler. Alternatively, the foot 2 and stem 6 may include 40% radiopaque filler or any other percent of radiopaque filler suitable to the application. For example, the foot 2 and/or stem 6 may include between about 10 and 50% radiopaque filler, or at least about 10, 20, 30, or 40% radiopaque filler.

Figure 2A:
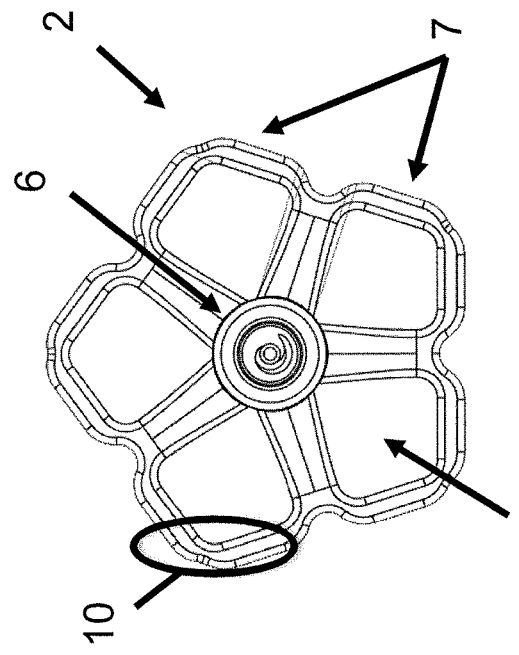
FIGS. 2A-2D illustrate one embodiment of a foot of a ventricular partitioning device.
Figure 2B:
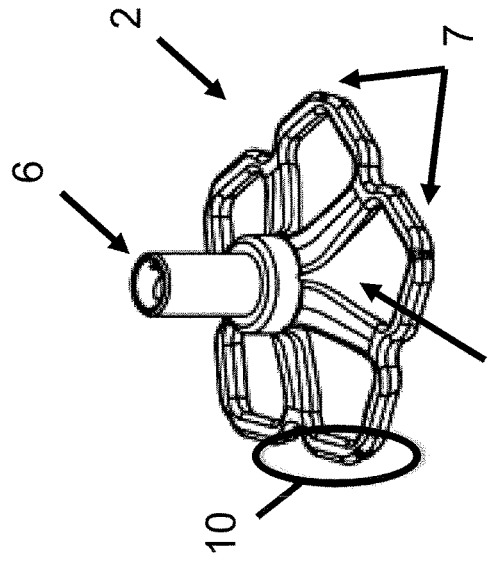
Figure 2C:
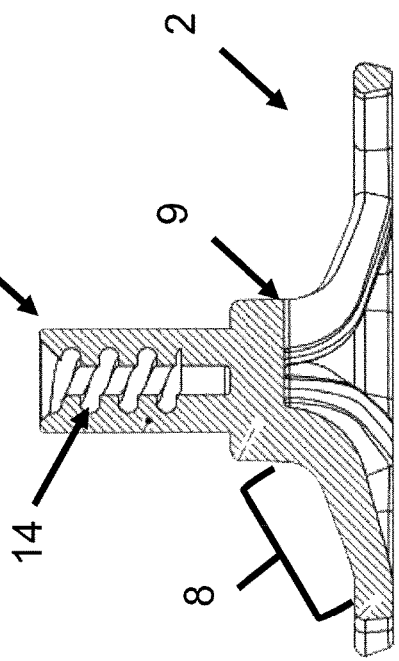
Figure 3A:
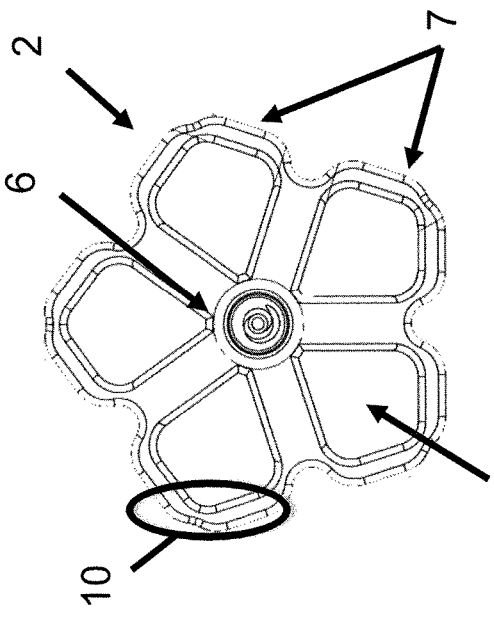
FIGS. 3A-3C illustrate an alternative embodiment of a foot of a ventricular partitioning device.
Figure 3B:
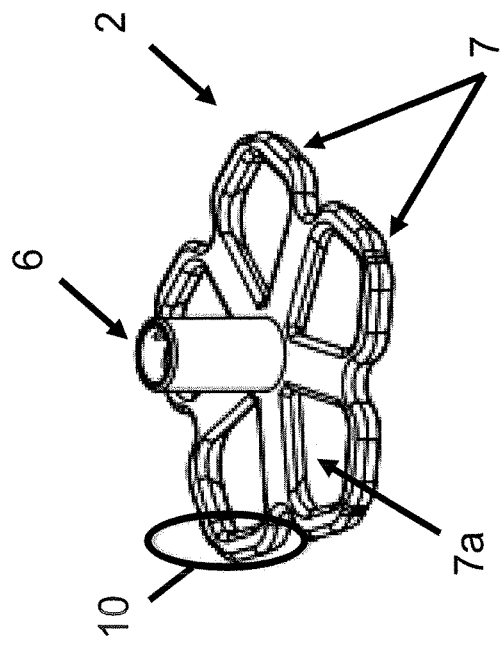
Figure 3C:
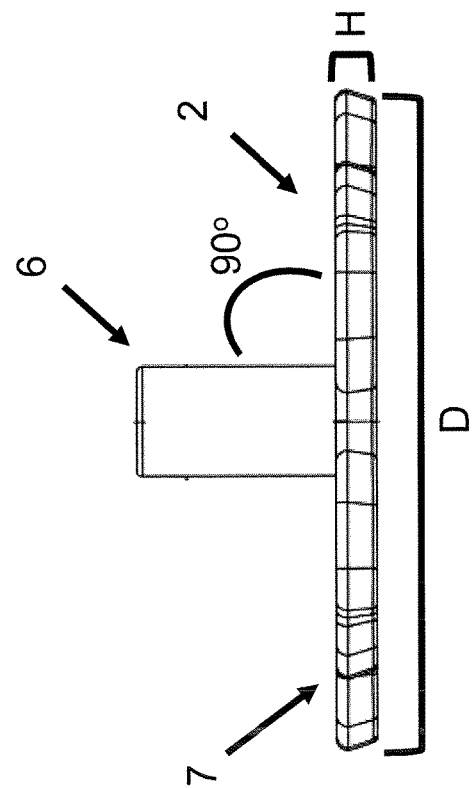

In some embodiments, as shown in FIGS. 2C and 3C, the foot 2 may have a height H ranging from 0.5 mm to 4.0 mm and a diameter D ranging from 13 mm to 17 mm, depending on the distance between the apex of the ventricle and the papillary muscle in the ventricle. In some embodiments, the foot 2 of the ventricular partitioning device may comprise a plurality of sections or petals 7. In some embodiments, a foot 2 may include 1, 2, 3, 4, 5, 6, 7, 8, 9, or 10 petals. In one embodiment, the foot 2 includes 5 petals, as shown in FIGS. 2A, 2B, 3A, and 3C. The petals 7 may include a looped configuration such that each petal includes an aperture 7a. Alternatively, the petals may comprise a solid configuration. Each petal 7 may be coupled to at least two other petals 7 of the foot 2 of the ventricular partitioning device. Alternatively, each petal 7 of the foot 2 may be separate and uncoupled from the other petals 7 of the foot 2. In some embodiments, the foot may alternatively include a screw for securing the ventricular partitioning device to the apex, a hub, or any other component suitable for positioning a ventricular partitioning device in a heart.

Figure 2D:
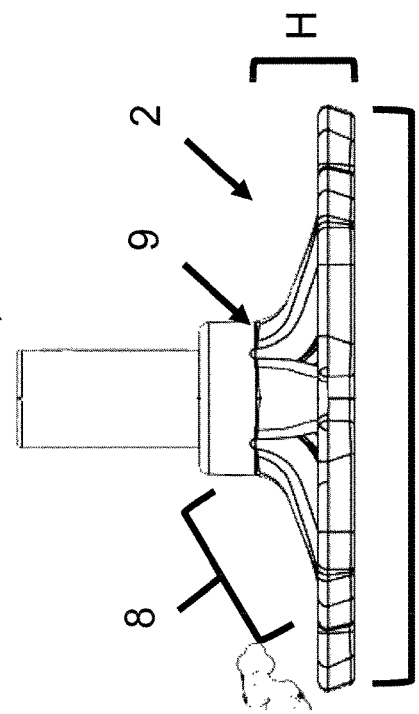

In some embodiments, as shown in FIGS. 2A, 2C, and 2D, the petals 7 of the foot 2 may be curved or include an angled portion 8, such that the point of attachment 9 of the petals 7 to the stem 6 is held at a distance from the apex of the ventricle while the perimeter 10 of the petals 7 is contacting the apex of the ventricle, as shown in FIGS. 2A and 2B. Alternatively, as shown in FIGS. 3A and 3C, the petals 7 may be coupled to the stem 6 at a right angle (90°) to the stem 6, such that the entire perimeter 10 and/or surface area of the petals 7 of the foot 2 may contact the apex of the ventricle.

In some embodiments, as shown in FIGS. 3A-3C, the foot 2 may be used in a ventricular partitioning device for treating acute myocardial infarction in order to prevent cardiac remodeling or damage (configured as an endocardial implant). In this embodiment, the device is configured to be positioned immediately adjacent to the heart wall, for example similar to a patch, across from the region of the infarct.

Figure 4B:
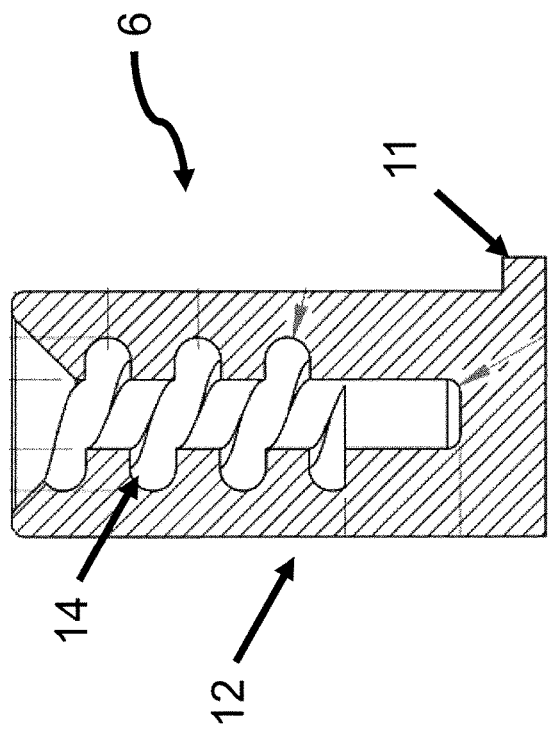
FIGS. 4A-4C illustrate one embodiment of a stem for coupling a membrane to a foot of a ventricular partitioning device.
Figure 4A:
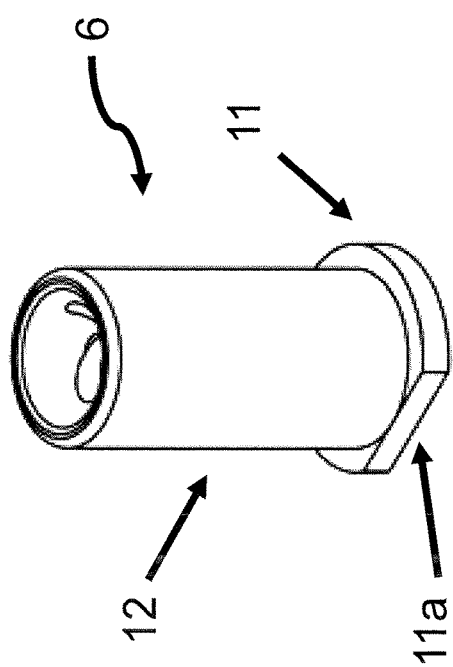
Figure 4C:
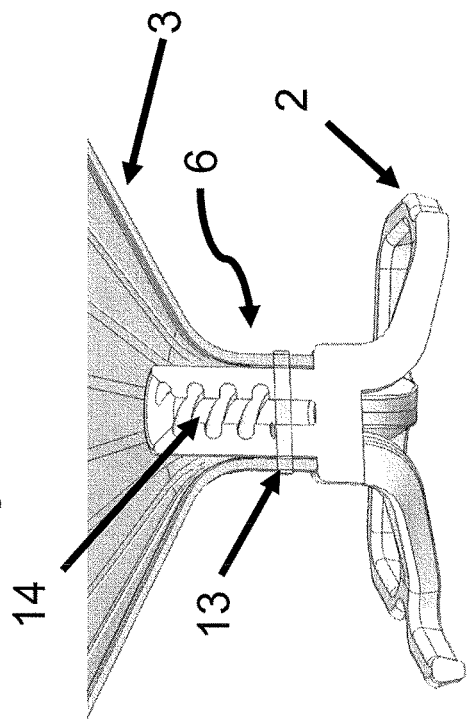

FIGS. 2A-3C illustrate a stem 6 coupled to a foot 2 of a ventricular partitioning device, such that the stem 6 is configured to receive a support frame of a ventricular partitioning device, as shown in FIG. 1. In some embodiments, the stem 6 may be substantially rigid for coupling to the support frame. However, the stem 6 may also be flexible for increasing the elastic recoil force of the ventricular partitioning device. The stem 6, as shown in FIGS. 4A-4C, may include a base 11 and a shaft 12 for receiving a support frame. In some embodiments, as shown in FIG. 4A, the base 11 may include a flange 11a to create a strong bond between the stem 6 and the foot 2 of the ventricular partitioning device. For example, the petals of the foot may be injection molded around the base of the stem and flange. Alternatively, in some embodiments, the stem 6 may be coupled to the foot 2 by another mechanism, for example by screwing, soldering, sintering, snapping, locking, fastening, or any other type of reversible or irreversible coupling mechanism.

FIGS. 4B-4C illustrate a cross-section of a stem 6 of a ventricular partitioning device in accordance with a preferred embodiment. The stem 6 may serve as an interface between the foot 2 and the support frame 3 of the ventricular partitioning device. As shown in FIG. 4C, the foot 2 may be secured to the support frame 3 by a cross pin 13 or any other type of fastener. For example, the hub or shaft at the base of the support frame may slide into the shaft 12 of the stem 6, such that a pin 13 may be inserted through the cross-section of the stem 6 to couple the support frame 3 to the stem 6. Alternatively, the support frame may be soldered, fastened, glued, or otherwise reversibly or irreversibly coupled to the stem. In some embodiments, the shaft 12 of the stem 6 may be configured to receive a delivery catheter, as described below in association with FIG. 10. For example, the shaft 12 may include helical grooves 14 such that a shaft of the delivery catheter may be screwed into the shaft of the stem 6, as shown in FIGS. 2D, 4B, and 4C.

Figure 5A:
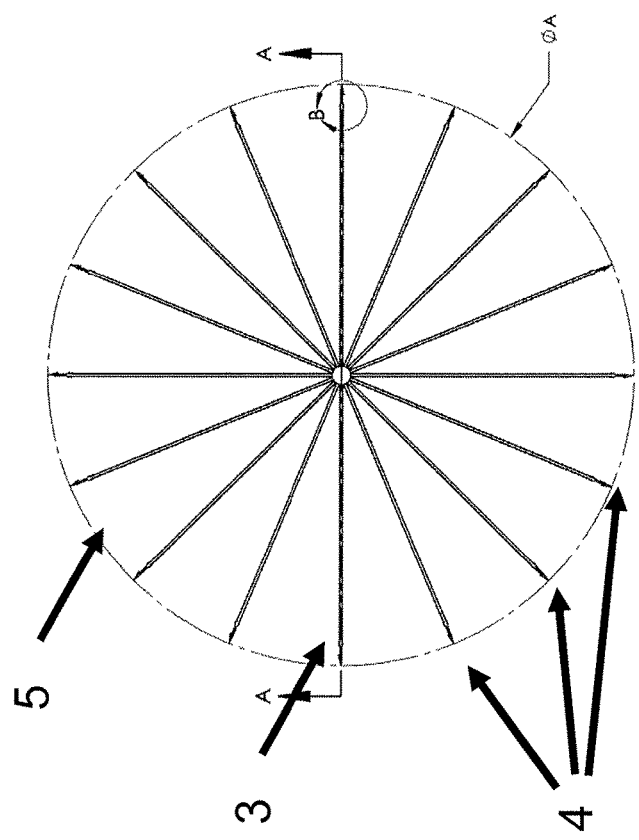
FIGS. 5A and 5B illustrate a top and side view of one embodiment of a membrane coupled to a support frame of a ventricular partitioning device, respectively.
Figure 5B:
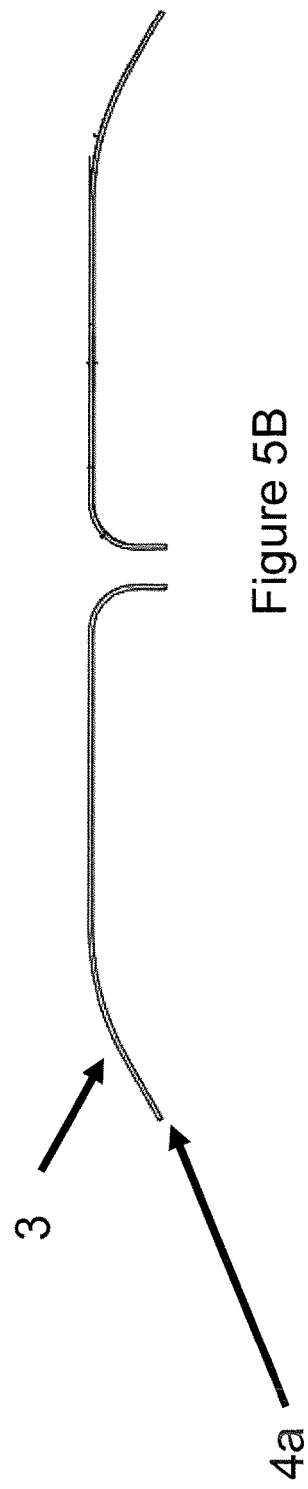

FIGS. 5A and 5B illustrate a top view and side view, respectively, of a membrane 5 coupled to a support frame 3 of a ventricular partitioning device in accordance with a preferred embodiment. The membrane 5 coupled to the support frame 3 is a pressure-receiving surface of the ventricular partitioning device, such that the elastic recoil force of the ventricle is improved when the ventricular partitioning device is implanted. The membrane 5 may be stretched over the struts to give the frame a disk like shape. The membrane 5 may include expanded Polytetrafuoroethylene (ePTFE) having a thickness between 0.01 mm and 1 mm. In one embodiment, the membrane has a thickness of about 0.08 mm. Alternatively, in some embodiments, the membrane 5 may include mesh, or other appropriate permeable, semi-permeable, or impermeable membranes. In some embodiments, the membrane 5 may be formed of a suitable biocompatible polymeric material including Nylon, PET (polyethylene terephthalate) and polyesters such as Hytrel. In some embodiments, the membrane 5 may be porous to facilitate tissue ingrowth after deployment within a patient's heart.

As shown in FIG. 5B, the first free ends 4a of the support frame 3 coupled to the membrane 5 may deflect away from the centerline axis of the ventricular partitioning device when the ventricular partitioning device is deployed in a ventricle. The deflection may improve the anchoring of the ventricular partitioning device to an interior wall of a ventricle.

In some embodiments, as shown in FIGS. 5A, 6A, and 6B, the support frame 3 may include a plurality of radially expandable struts 4. The struts 4 may be configured to support a membrane 5 coupled to the struts. The struts 4 may improve the elastic recoil properties of the membrane 5 coupled to the struts 4. In some embodiments, the struts 4 may be configured for anchoring the ventricular partitioning device to an interior wall of the ventricle. In some embodiments, the support frame 3 may include 5 struts, 10 struts, 15 struts, or 20 struts. In one embodiment, the support frame 3 includes 16 struts. In some embodiments, each strut 4 may be 1 to 8 cm in length. In one embodiment, each strut 4 has a length of about 3 to 6 cm. In some embodiments, the support frame 3 may be smoothed to a particular surface roughness to reduce trauma to the patient during delivery and improve characteristics of the ventricular partitioning device, such as corrosion resistance and durability. The support frame 3 may be electropolished, chemically treated, and/or mechanically polished by a wheel, tumbling, abrasion, sand blasting, chemical etching, and/or any other method of polishing to achieve a particular surface roughness. In some embodiments, the roughness average (Ra) of the support frame may be between 0.01 μm and 1 μm. In one embodiment, the roughness average (Ra) of the support frame is between about 0.85 μm and 0.15 μm.

In some embodiments, as shown in FIGS. 6A-6C, each strut 4 of the support frame 3 may include a first free end 4a and a second end 4b coupled to the foot. The first free end 4a of the support frame 3 may include an anchor or barb 15 for coupling the support frame 3 to an interior wall portion of a heart. This anchoring may allow the ventricular partitioning device to contract and relax with each systolic and diastolic phase, respectively, of the heart cycle. Further, the anchoring may partition the heart into functional and non-functional portions, such that the non-functional portion is proximal to the foot of the ventricular partitioning device.

In some embodiments, as shown in FIGS. 6A-6C, a stop 16 may be located at or near the base of the anchors 15 proximal to the first free end 4a of the struts 4. The stop 16 may be a bulge, projection, or otherwise widening of a portion of the strut 4 near the first free end 4a, which serves to lock the support frame 3 in place and/or reduce or prevent over-penetration of the struts 4 into the ventricle wall. The length of the struts 4 may alternate between a short length strut and a long length strut so that the anchors 15 and/or stops 16 are staggered, which allows the struts 4 to be collapsed into a more compact diameter for delivery.

In some embodiments, as shown in FIG. 6A, each first free end 4a of the strut 4 of the support frame 3 may further include an eyelet 16a. The eyelet 16a may serve as a stop 16, as described above, and/or as a mechanism to couple the membrane to the support frame. During manufacturing, polymer may be melted near the eyelet 16a of the support frame 3 to couple the membrane to the support frame, such that the melted polymer may flow from one side of the strut 4 through the eyelet 16 to the other side of the strut 4 to couple the membrane to the struts 4. As shown in an alternative embodiment in FIGS. 6B-6C, the stop 16, as described above, may be manufactured without an eyelet, such that the polymer melts around the stop 16 and secures the membrane to the support frame 3.

Figure 7A:
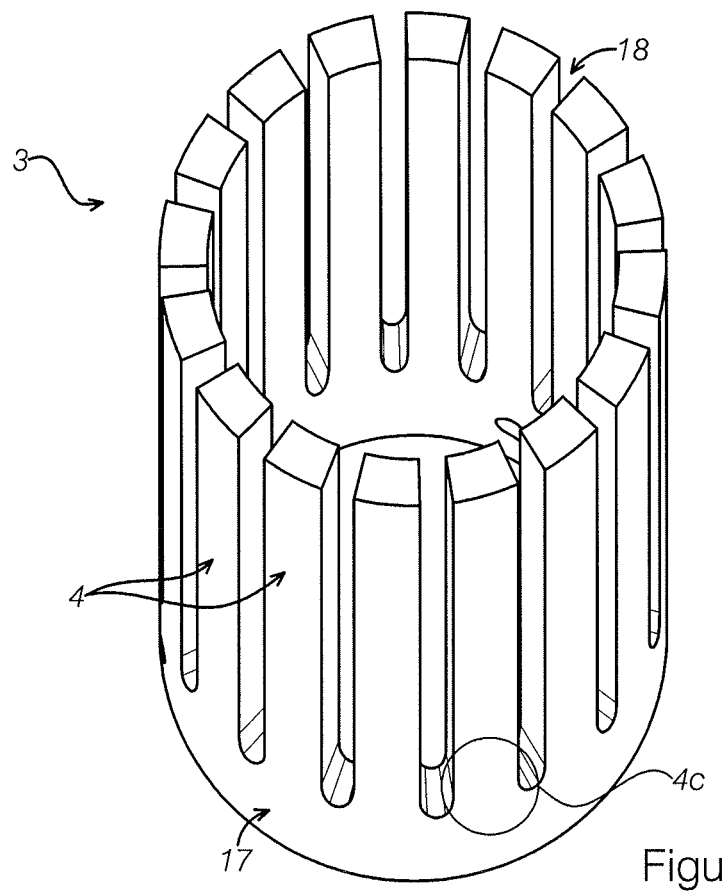
FIGS. 7A-7D illustrate one embodiment of a support frame.

In some embodiments, as shown in FIGS. 7A-7D, the struts may include a material such as, for example, Nitinol, stainless steel, titanium alloys, NiTi alloy, other metal alloys, or plastic composites. In some embodiments, the struts 4 and/or support frame 3 may include a material, which allows for compression of the first free ends towards the central axis during delivery and self expansion upon deployment of the ventricular partitioning device in a patient's heart. In some embodiments, the struts 4 and/or support frame 3 may be cut, for example by a laser, from a tube including Nitinol, stainless steel, or a similar material. During manufacturing, a plurality of longitudinal cuts may extend from one end of the metal tube to a position offset from the other end of the tube, leaving a hub 17 from which the struts 4 extend. The cuts may result in a plurality of slots 18 between the struts 4. In some embodiments, as shown in FIG. 7A, the spacing between the slots 18 may define the strut width W while the thickness of the tube may define the strut thickness T. In some embodiments, the spacing of the slots 18 around the tube may result in struts 4 having a cross-sectional width that is slightly greater than its cross-sectional thickness. This may be accomplished by the slot 18 having a slightly greater spacing than the thickness of the tube. In some embodiments, slightly greater may mean about 1, 2, 3, 4, 5, 10, 15, 20, or 25 percent, or may mean between about 1 to 25 percent, or may mean between about 5 to 20 percent.

Figure 7B:
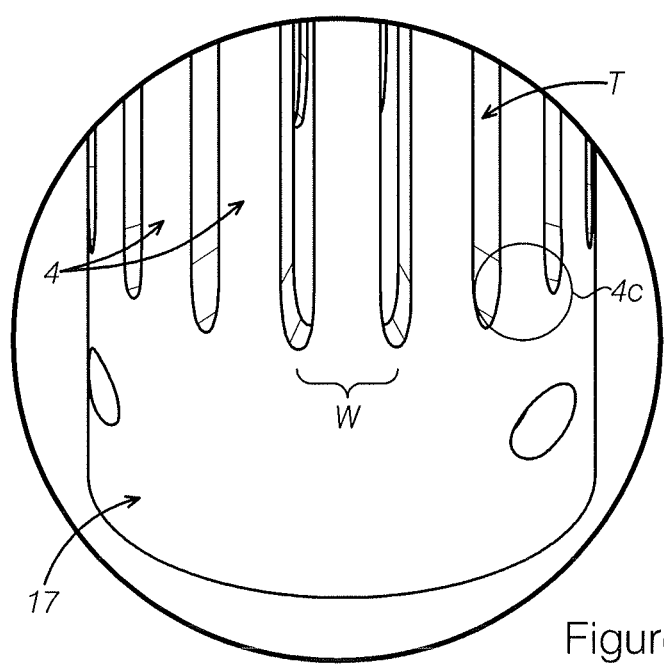

In some embodiments, as shown in FIG. 7B, the base 4c of the strut 4 is the second end of the strut that couples to the foot and extends from the hub 17. The base 4e of the strut 4 may be flared such that the width of the strut 4 increases as it approaches the hub 17. In some embodiments, the flared base 4c may spread bending strains over a larger amount of material, thereby decreasing peak strains during manufacturing, loading of the implant within a catheter, and cyclical use in the ventricle after implantation. In some embodiments, the width of the strut 4 at the hub 17 may be about 5 to 25 percent larger than the width of the strut 4 at a middle portion of the strut 4. In some embodiments, the length of the flared base 4c may be about equal to the width of the flared base 4c at the hub 17. Alternatively, the length of the flared base 4c may be greater than about 5, 10, 15, 20, 25, 30, 35, 40, 45, 50, 75, 100, or 200 percent of the width of the flared base 4c at the hub 17. Alternatively, the length of the flared base 4e may be less than about 95, 90, 85, 80, 75, 70, 65, 60, 55, or 50 percent of the width of the flared base 4c at the hub 17. The flared base may be formed by tapering the slot as it reaches the hub.

Figure 7C:
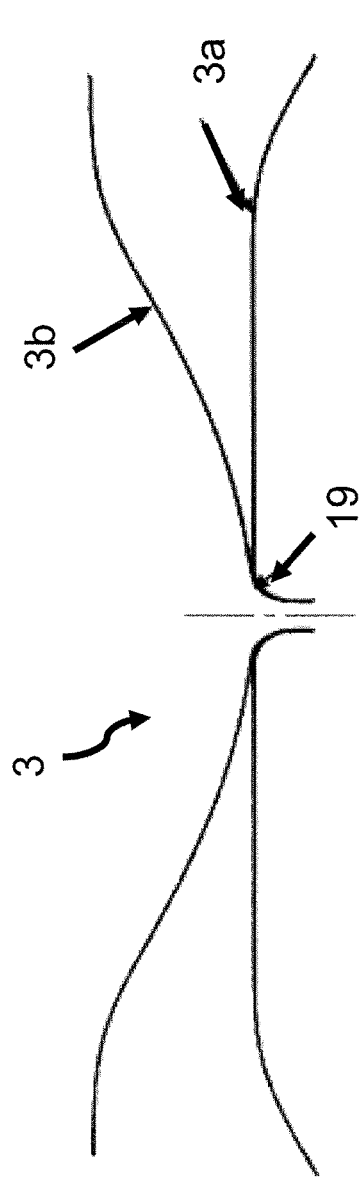

As illustrated in FIG. 7C, in some embodiments, the flared base can have a base bend radius 19 that is sized to (1) reduce or limit peak strains during shape setting to reduce or prevent damage and cracking of the metal frame; (2) reduce or limit peak strains when the implant is loaded into the catheter and reduce or prevent plastic deformation of the metal; and (3) reduce or minimize the height of the implant. In some embodiments, the diameter of the support frame 3 in its free shape 3a can be slightly oversized relative to its laminated shape 3b so that the membrane will stay tight after lamination. For example, the support frame 3 can be oversized by about 3, 4, 5, 6, or 7 mm, or be oversized between about 2 to 10 mm. The lamination mold is designed to conform to the natural shape of the support frame 3 when it is reduced to the lamination diameter 3b. This ensures that the support frame 3 is free to move as designed with little or no alternating strain concentrations.

Figure 7D:
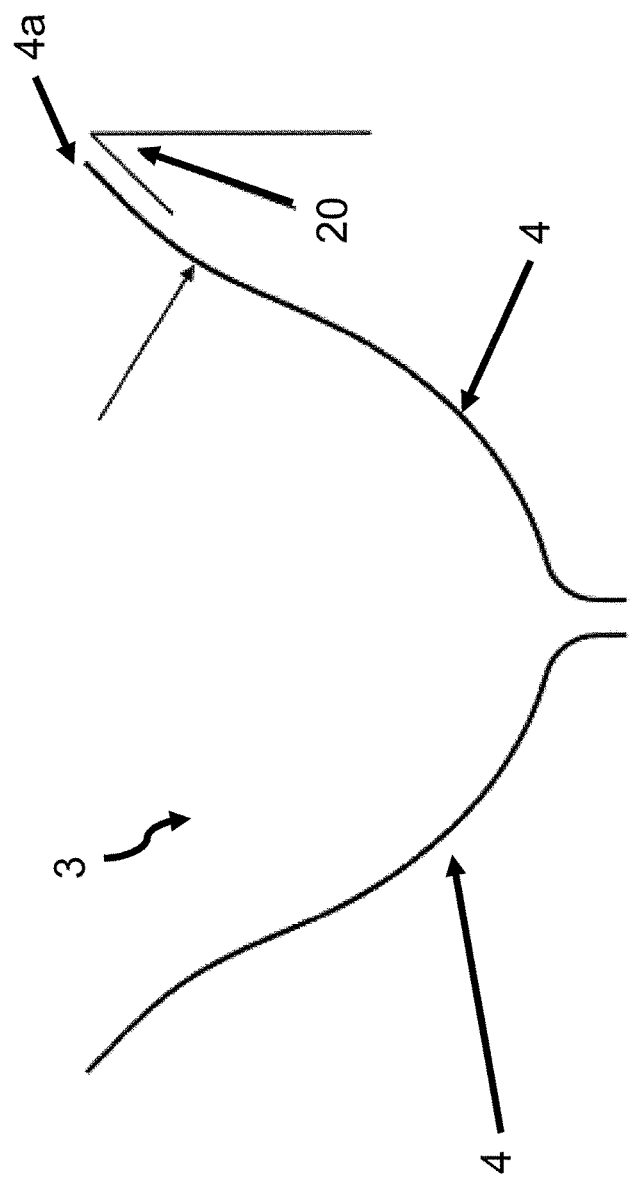

As shown in FIG. 7D, after lamination, there is a strut curvature 20 near the anchor on the free ends 4a of the struts 4 that is designed to optimize the angle of engagement with the left ventricle wall, which improves retention of the implant in the left ventricle. In some embodiments, the strut curvature 20 has a radius of about 0.5 to 1.5 inches. In some embodiments, the angle of engagement is about 30 to 60 degrees.

In some embodiments as described above, the strut cross-section dimensions having a width slightly greater than the thickness, in conjunction with the flared base, may bias the strut so that it deflects outwardly without any significant twist. This may improve the strength of the struts and reduce strain.

Loading and Delivery Systems

Figure 11:
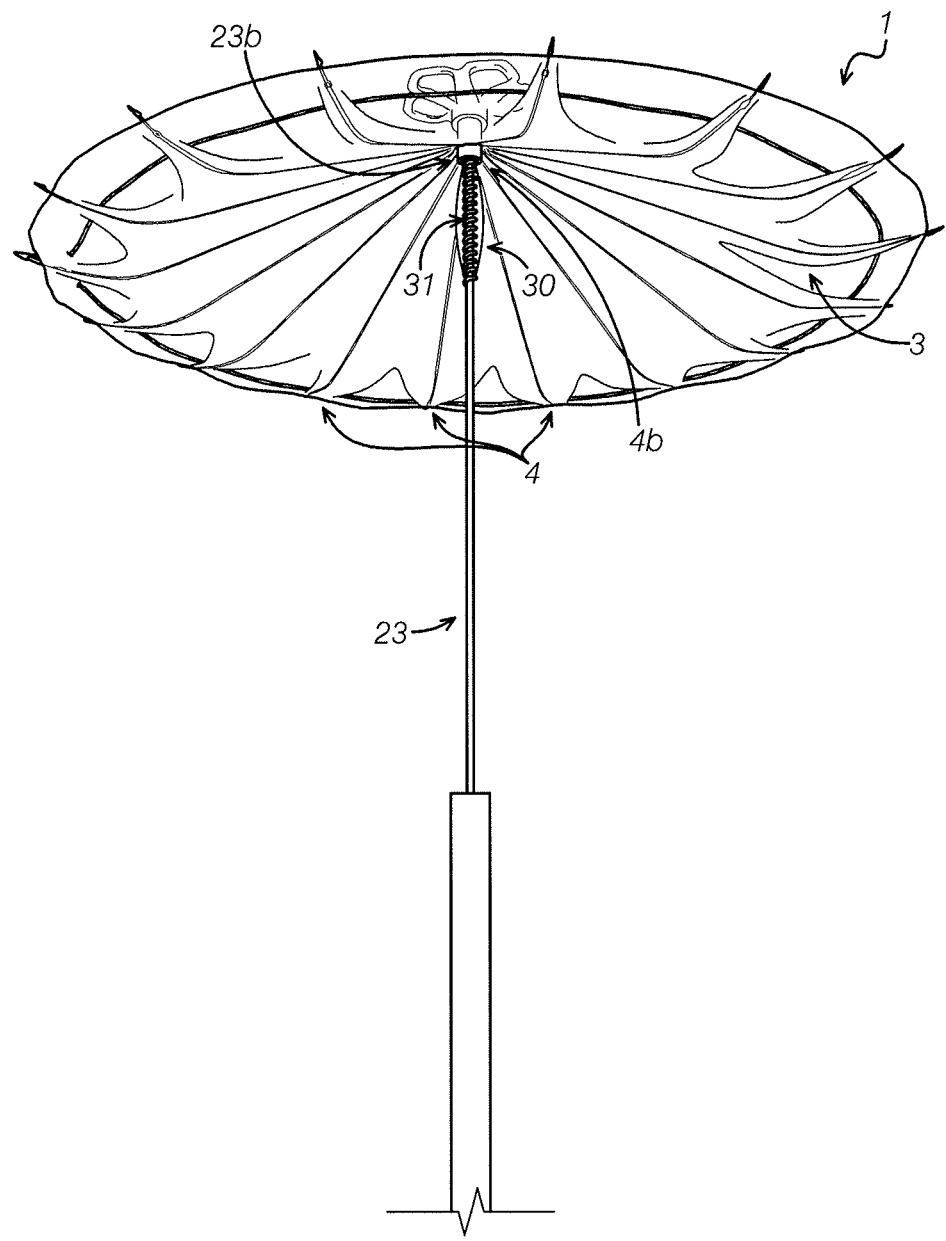
FIG. 11 illustrates one embodiment of a delivery catheter coupled to a ventricular partitioning device.

In some embodiments, a delivery system for a ventricular partitioning device may include an implant loading system, which collapses the ventricular partitioning device into a substantially linear delivery configuration for passage into a guide catheter and into a heart, and which expands the ventricular partitioning device into an umbrella-like shape once the device is delivered into a heart. In some embodiments, the ventricular partitioning device may be delivered transapically, percutaneously, endovascularly, or through any other appropriate means or procedure. In some embodiments, the ventricular partitioning device is coupled to a delivery catheter to facilitate loading into the guide catheter. In some embodiments, the ventricular partitioning device is coupled to a shaft disposed in a lumen of the delivery catheter, for example by screwing the ventricular partitioning device to a shaft in a lumen of the delivery catheter, as shown in FIG. 11.

Described below are two different embodiments of an implant loading system for loading a ventricular partitioning device into a guide catheter. The system as shown in FIGS. 8A-9C requires fewer steps and components as compared to the implant loading system described in FIGS. 10A-10D. However, as evident to one of skill in the art, both implant loading systems may be used to load a ventricular partitioning device into a lumen of a guide catheter for delivery to a heart of a patient.

Figure 8A:
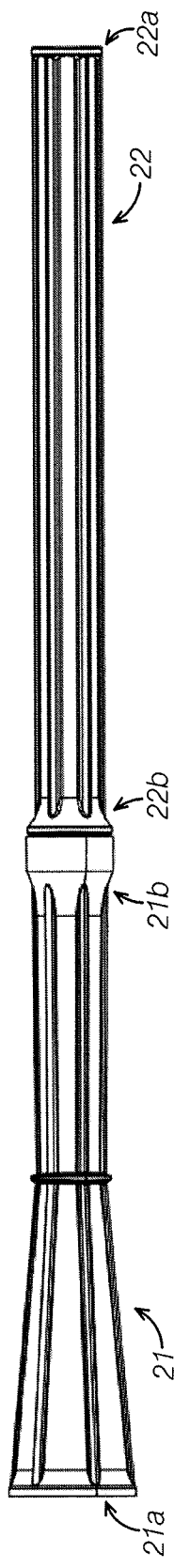
FIGS. 8A-8D illustrate an exterior view of one embodiment of an implant loading system for a ventricular partitioning device.
Figure 8B:
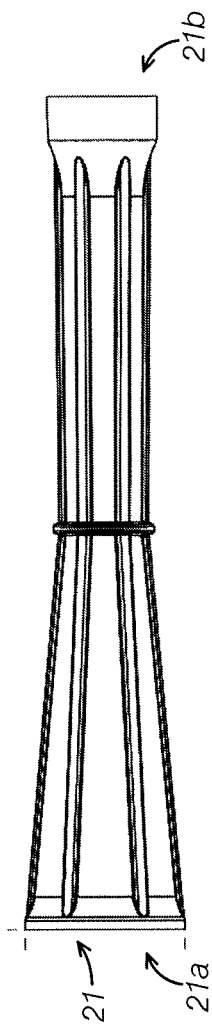
Figure 8C:
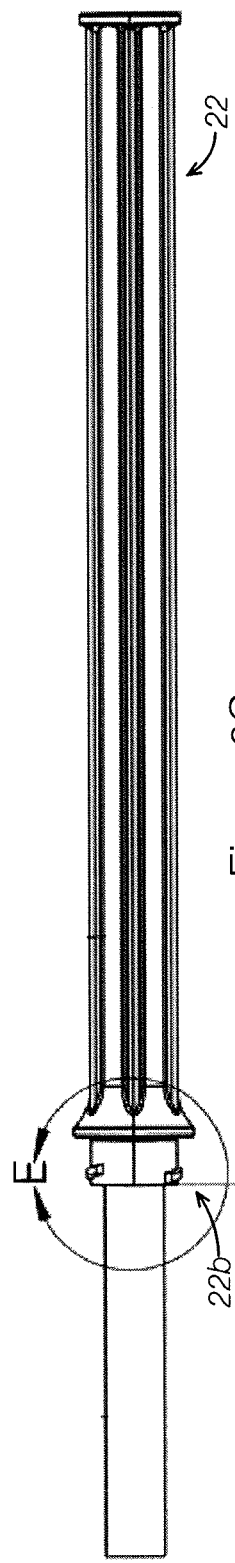
Figure 8D:
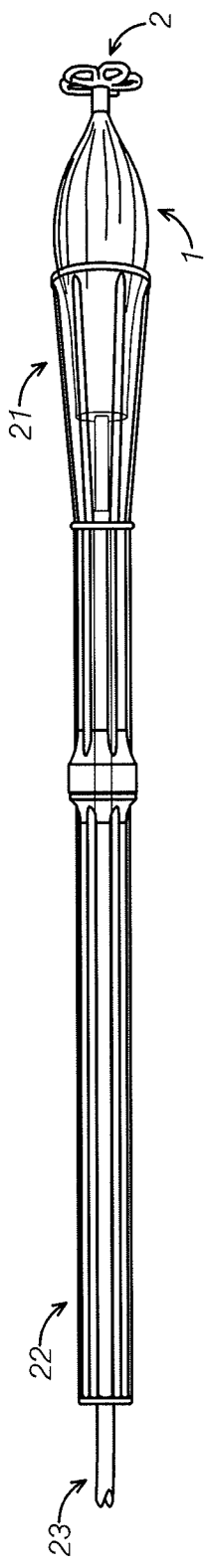

In some embodiments, as shown in FIGS. 8A-9C, an implant loading system for a ventricular partitioning device may include a funnel 21 with a flared first end 21a and a second end 21b, wherein the flared first end 21a is configured for receiving a collapsed ventricular partitioning device 1, as shown in FIGS. 8B and 8D, and a sleeve 22 removably coupled to the second end 21b of the funnel 21, such that the sleeve 22 is configured to transfer the ventricular partitioning device 1 to a guide catheter, as shown in FIGS. 8C and 8D.

FIGS. 8A-8D and 9A-9C illustrate an exterior and cross-sectional view, respectively, of an implant loading system for a ventricular partitioning device, in accordance with a preferred embodiment. As shown in FIGS. 8A-8D, a ventricular partitioning device 1 may be coupled to a delivery catheter 23, as described below. The ventricular partitioning device 1 may be collapsed by drawing at least two sutures, strings, ties, or threads together, such that the diameter of the membrane and thus the ventricular partitioning device is reduced. In this manner, the ventricular partitioning device 1 may be at least partially collapsed around the delivery catheter 23. As used herein, "two sutures, strings, ties, or threads" may refer to two separate sutures, strings, ties, or threads, or two separate ends of a looped suture, string, tie, or thread. In some embodiments, the at least two sutures may be coupled by a tab, such that both sutures may be tensioned and the ventricular partitioning device at least partially collapsed by manipulating the tab.

In some embodiments, the ventricular partitioning device may be positioned in the flared first end 21a of the funnel 21 with the first free ends of the struts of the ventricular partitioning device entering the flared first end 21a of the funnel 21 followed by the foot 2 of the ventricular partitioning device, as shown in FIG. 8D. The funnel 21 may function to fully collapse the ventricular partitioning device for advancement into a lumen of a guide catheter. In some embodiments, as shown in FIG. 8A, the second end 21b of the funnel 21 is removably coupled to a second, distal end 22b of a sleeve 22, for example by threading 24 the funnel 21 onto the second, distal end 22b of the sleeve 22, as shown in FIGS. 8A and 8C. One embodiment of the threads 24 for coupling the funnel 21 to the sleeve 22, as shown in FIG. 9B, is evident using a cross-sectional view of the funnel 21 and sleeve 22, such as shown in FIGS. 9A and 9C. Alternatively, the funnel 21 may be coupled to the sleeve 22 by any suitable mechanism. In some embodiments, the ventricular partitioning device coupled to the delivery catheter 23 may be advanced through the funnel 21 into the sleeve 22 for loading of the ventricular partitioning device into a lumen of a guide catheter. The first, proximal end 22a of the sleeve 22 may include a stop or tapering of the sleeve, such that the ventricular partitioning device does not protrude from the first, proximal end 22a of the sleeve 22 or extend out of the first end 22a of the sleeve 22, as shown in FIGS. 8A-8C. In some embodiments, the interior of the funnel 21 and sleeve 22 may include a smooth surface, for example without flashes or burrs, such that the ventricular partitioning device is not torn or scratched during loading, unloading, and advancing. Once, the ventricular partitioning device is advanced into the sleeve 22 from the funnel 21, the funnel 21 may be uncoupled from the second, distal end 22b of the sleeve 22 and the guide catheter may be coupled in its place.

Figure 12A:
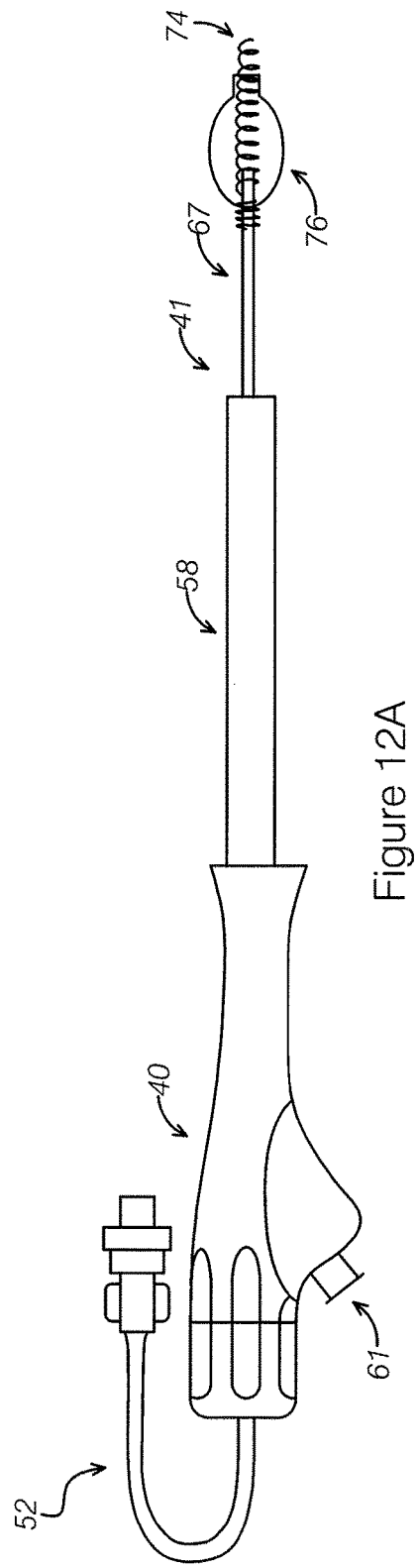
FIG. 12A illustrates one embodiment of a delivery catheter.
Figure 14:
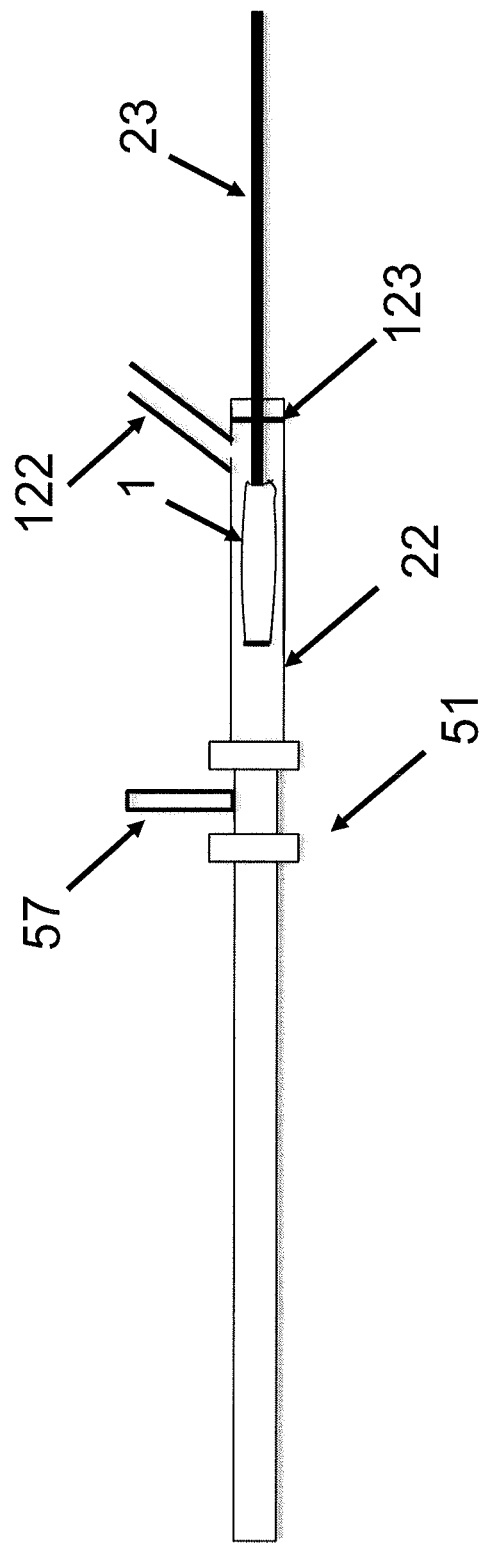
FIG. 14 illustrates another embodiment of a delivery system.

Further, as shown in FIG. 14, in some embodiments, the sleeve 22 may include a fluid delivery port 122, such that fluid, for example saline, may be injected into the sleeve, as described in further detail below. In some embodiments, the fluid is substantially prevented or inhibited from exiting the first or proximal end of the sleeve by a mechanical seal 123 coupled to the first or proximal end 22a of the sleeve 22. The mechanical seal 123 may be, for example, a gasket, O-ring, bung comprising an aperture, bodok seal, hermetic seal, diaphragm seal, labyrinth seal, rotating hemostatic valve, or any other suitable sealing mechanism. For example, as shown in FIG. 12F, the mechanical seal 80 may be a rotating hemostatic valve, which can be rotated to adjust the size of the valve aperture to maintain hemostasis while allowing passage of the delivery catheter and implant through the valve and into the sleeve 22 and guide catheter. In various embodiments, the mechanical seal 123 is sized to contact an inner surface of the sleeve and an outer surface of the delivery catheter 23 to form a liquid-tight or fluid-tight seal. Alternatively, the mechanical seal may be positioned and formed so as to create a liquid-tight or fluid-tight seal by any mechanism known to one skilled in the art. The mechanical seal 123 may be adhered, fastened, or otherwise coupled to the sleeve 22 using any suitable attachment mechanism. Alternatively, the mechanical seal may be integrally molded or otherwise formed with the sleeve.

Figure 15A:
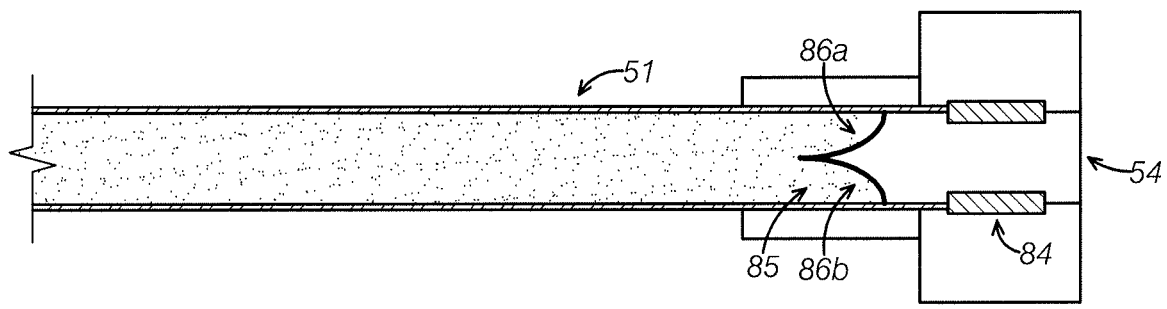
FIG. 15B illustrates one embodiment of a delivery catheter inserted into a guide catheter through two hemostatic valves.
Figure 15B:
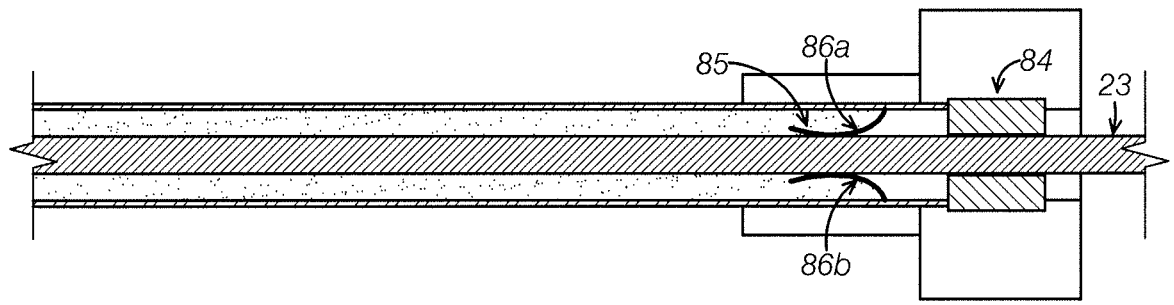

In some embodiments, for example as shown in FIGS. 15A and 15B, the distal end 22b of the sleeve 22 may be coupled to a guide catheter 51. In some embodiments, the distal end 22b of the sleeve 22 may be coupled to a guide catheter 51 using a valve 84, such as a hemostatic valve. The valve 84 may be positioned in the sleeve 22, in the guide catheter 51, or in a separate joint coupling the sleeve 22 to the guide catheter 51, for example a joint (e.g., T-port) comprising a fluid delivery port 57. In some embodiments, the valve 84 may be a rotating valve, which is configured to rotate to increase or decrease the size of the aperture in the valve 84 to allow the passage of the delivery catheter 23 and implant 1 or other medical device through the valve 84 while maintaining a fluid-tight seal around the delivery catheter 23. In some embodiments, the guide catheter 51 can also include a fluid delivery port 57 for introducing fluid into guide catheter.

Additionally or alternatively, in some embodiments, as shown in FIGS. 15A and 15B, the coupling between the guide catheter 51 and the sleeve 22 further includes a second hemostatic valve, such as a check valve or duck-bill valve 85, to reduce or prevent backflow before the delivery catheter 23 is inserted into the guide catheter 51 and the valve is empty. In some embodiments, the check valve or duck-bill valve 85 forms a portion of the guide catheter 51; in other embodiments, the check valve or duck-bill valve 85 forms a portion of a separate joint (e.g., T-port) coupling the sleeve 22 to the guide catheter 51. In some embodiments, the check valve or duck-bill valve 85 covers or seals a proximal end 54 of the guide catheter 51. In one such embodiment, one end of the valve stretches over the proximal end 54 of the guide catheter 51, conforming to its shape, and a second end extends distally into the guide catheter 51. In some such embodiments, a first flap or side 86a and a second flap or side 86b of the check valve or duck-bill valve 85 form complementary surfaces that interlace or interweave when a delivery catheter is not present, as shown in FIG. 15A, and are displaced or splayed open when a delivery catheter is present, as shown in FIG. 15B. In some embodiments, the check valve or duck-bill valve comprises elastic or stretchable material, such that it conforms to the surface of the device or catheter extending through the valve. In some such embodiments, the check valve or duck-bill valve comprises rubber or synthetic elastomer.

The ventricular partitioning device may be advanced from the sleeve into the lumen of the guide catheter. In some embodiments, the delivery catheter 23 coupled to the ventricular partitioning device may be advanced through the guide catheter lumen into a heart of a patient to position the ventricular partitioning device in the heart of the patient. In some embodiments, the sleeve may be removed from the delivery catheter by any suitable mechanism after advancing the ventricular partitioning device into the lumen of the guide catheter. Alternatively, the delivery catheter may be lengthened such that the sleeve may remain on the delivery catheter while the ventricular partitioning device is being positioned in a heart of a patient.

Alternatively, in some embodiments as shown in FIGS. 10A-10D, an implant loading system for a ventricular partitioning device may further include a loader 24 comprising a lumen housing a two-piece introducer 25, referred to herein as a loader introducer pair. Instead of a two-step loading procedure, as shown in FIGS. 8A-9C, the loading procedure shown in FIGS. 10A-10D includes at least two more steps. In some embodiments, as show in FIG. 10A, the funnel 26 for loading the ventricular partitioning device into the sleeve 27 may be truncated as compared to the funnel 21 shown in FIG. 8B. Similar to FIGS. 8A and 8D, the tapered end 26b of the funnel 26 may be coupled to the second end 27b of the sleeve 27 and the ventricular partitioning device coupled to the delivery catheter may be advanced from the funnel 26 into the sleeve 27. In some embodiments, as shown in FIG. 10C, once the ventricular partitioning device is collapsed and advanced through the funnel 26 into the sleeve 27, the funnel 26 may be uncoupled from the second end 27b of the sleeve 27 and the second end 24b of the loader introducer pair 24/25 may be coupled to the second end 27b of the sleeve 27. The loader introducer pair 24/25 may be coupled to the sleeve 27 by a helical screw, latching, snapping, fastening, or any other type of coupling mechanism. The first end 24a of the loader introducer pair 24/25 may be coupled to a guide catheter, such that the lumen of the loader introducer pair is continuous with the lumen of the guide catheter. In some embodiments, as shown in FIG. 10C, the coupling mechanism may include a slot 28 on the loader 24 and a pin, knob, protrusion, or port on the guide catheter, such that the slot 28 receives the pin or port and secures the loader 24 to the guide catheter. Alternatively, the loader 24 may be coupled to the guide catheter by a helical screw, snapping, latching, or any other type of coupling mechanism.

As shown in FIG. 10C, the ventricular partitioning device may be advanced from the sleeve 27 into the loader introducer pair 24/25 and into the guide catheter. The loader 24 may be removed from the system by moving the introducer 25 and delivery catheter through a longitudinal slot 29 in the loader 24. The introducer 25 may be removed from the system by tearing or axially pulling apart the two halves 25a/25b of the introducer 25, as shown in FIG. 10D, such that the delivery catheter coupled to the ventricular partitioning device in the lumen of the guide catheter remains. In some embodiments, the sleeve 27 may remain on the delivery catheter or be removed. While two embodiments of an implant loading system are described above, any other suitable mechanism may be used and/or substituted by one skilled in the art to deliver a ventricular partitioning device to a heart of a patient.

In some embodiments, as shown in FIG. 11, a system for treating heart failure may include a ventricular partitioning device as described above, and a delivery catheter 23 having a proximal end and a distal end 23b. Further, a system for treating heart failure may include an expansion member 30 near the distal end 23b of the delivery catheter 23 configured to apply pressure to the support frame 3 of the ventricular partitioning device 1 to move the ventricular partitioning device 1 from a collapsed delivery configuration to an expanded deployed configuration, and a coupling element 31 configured to secure the expansion member 30 to the ventricular partitioning device 1 during deployment.

In some embodiments, the expansion member 30 is coupled to the ventricular partitioning device 1 by a coupling element 31 proximal to the second ends 4b of the struts 4 of the support frame 3. In some embodiments, the coupling element 31 includes a helical screw, as shown in FIG. 11. Alternatively, in some embodiments, the coupling element 31 may include a sliding latch, lock, hook, or any other suitable mechanism. In some embodiments, the expansion member 30, for example a balloon, may be in fluid communication with a lumen in the shaft of the delivery catheter 23, such that inflation fluid may be delivered to the interior of the expansion member 30 to inflate the balloon. Alternatively, the balloon may be inflated by a gas, gel, or any other material. The balloon, once inflated, may include a diameter between 30 mm and 45 mm. In one embodiment, the balloon, once inflated, has a diameter of more than or equal to 32 mm.

In some embodiments, the ventricular partitioning device 1 radially expands in the ventricle once delivered to the ventricle. The expansion member 30, coupled to the ventricular partitioning device 1 by a coupling element 31, may be inflated at the distal end of the delivery catheter 23 to fully expand the ventricular partitioning device 1 within the ventricle and to facilitate anchoring the struts 4 of the ventricular partitioning device to an interior wall of the ventricle. Alternatively, in some embodiments, the ventricular partitioning device 1 may expand and anchor sufficiently without the use of the expansion member 30. In some embodiments, rotation of the delivery catheter 23 coupled to the ventricular partitioning device 1 may remove the expansion member 30 and delivery catheter 23 from the ventricular partitioning device 1.

In some embodiments, a delivery system for an implantable ventricular partitioning device includes a delivery catheter, a sleeve, a first fluid delivery port, and a guide catheter. Such devices may include any or all of the features described in the embodiments provided above. In some embodiments, such as shown in FIGS. 12-13, the delivery catheter 52 is formed of a tubular body, or shaft, includes a proximal end and a distal end, and is configured to couple to a ventricular partitioning device or other implantable device. The implant loader sleeve 22 of various embodiments defines a lumen configured to receive the delivery catheter 52 and the implantable device, as previously described above. In some embodiments, the first fluid delivery port 61 is positioned on the delivery catheter 52, as illustrated in FIG. 12A, and/or a fluid deliver port can be located on the sleeve 22, as shown in FIG. 14, and a mechanical seal 42 is coupled to the sleeve 22. For example, the mechanical seal 42 can be a gasket or other sealing device, as further described herein, that is located in the proximal end of the sleeve 22. The mechanical seal 42 of some embodiments is sized to contact an inner surface of the sleeve 22 and an outer surface of the delivery catheter 52 to form a liquid-tight seal. In some embodiments, the guide catheter 51 is formed of a tubular body having a proximal end, a distal end, a lumen extending therethrough for receiving the delivery catheter 51, and a second fluid delivery port 57 positioned thereon. In various embodiments, the proximal end of the guide catheter 51 is connected to the distal end of the sleeve 22. In some embodiments, the fluid delivery ports can be opened and closed by, for example, using a valve or by clamping the lines supplying fluid to the ports.

The system, as shown in FIGS. 12-13, functions to maintain the implantable device (e.g. ventricular partitioning device) relatively free of blood during implantation, reduce or prevent the flow of blood back into the delivery system during implantation of the ventricular partitioning device, reduce friction between the ventricular partitioning device and the delivery system, and/or facilitate easy opening of the ventricular partitioning device in the ventricle.

In some embodiments, delivering fluid through the first and/or second fluid delivery ports, for example at a positive pressure, creates a first pressure in the guide catheter that is greater than a second pressure in the ventricle. Such fluid delivery is shown with two fluid delivery arrows in FIG. 12B. The resulting increased pressure in the guide catheter may reduce or prevent blood from flowing backward into the guide catheter and onto the ventricular partitioning device. It has been found that in at least some embodiments, deployment of the device in the ventricle is achieved more easily with more consistent and effective results when it does not get loaded down with blood during the implantation process.

In some embodiments, the positive pressure of fluid delivery is about 150-200, 200-250, 250-300 mm Hg, or any other suitable pressure. In some embodiments, the first pressure is between 200 and 600 mm Hg, and preferably 200-400 mm Hg, and the second pressure is between 0 and 300 mm Hg, and preferably 75-175 mm Hg. In some embodiments, the first pressure is about 200-250, 250-300, 300-350, 350-400, 400-450, 450-500, 500-550, or 550-600 mm Hg, and the second pressure is about 5-100, 100-150, 150-200, 200-250, or 250-300 mm Hg. In one embodiment, the first pressure is about 300 mm Hg and the second pressure is about 120 mm Hg. In some embodiments, the fluid can be delivered at a positive pressure using a pressurized fluid reservoir, such as a pressurized IV bag, for example.

Alternatively, in some embodiments, the fluid can be delivered at a predetermined rate using a pump. The flow rate of fluid through the catheter can be about 30-120 mL/min, or about 0.5-5 mL/sec, or about 0.5, 1.0, 1.5, or 2.0 mL/sec. In some embodiments, the flow rate can be adjusted by the operator.

In some embodiments, the injection of fluid through the first and/or second fluid delivery ports may alternatively or additionally function to remove bubbles from the delivery system. For example, the first fluid delivery port of the delivery catheter can be used to introduce fluid while the second fluid delivery port, which can be located on the guide catheter, can be used to aspirate any trapped gas bubbles. Generally, the bubbles can be aspirated using a fluid delivery port that is distal to the implant. Alternatively, the delivery system as described may be used in any suitable catheterization and/or implantation procedure or method.

As shown in FIGS. 12A and 13, the delivery catheter 52 includes a proximal end 40 and a distal end 41. The distal end 41 of the delivery catheter 52 is configured to couple to an implantable device, for example a ventricular partitioning device, as described above. In some embodiments, the delivery catheter 52 has an outer shaft 58 with an interior (i.e., lumen) 59, and an adapter 60 at a proximal end with a first fluid delivery port 61. The first fluid delivery port 61 is in fluid communication with the interior 59 of the outer shaft 58 of the delivery catheter for delivery of fluid, for example heparinized saline, into the delivery system. Alternatively, in some embodiments, the first fluid delivery port may be positioned on the sleeve configured to receive the implantable device coupled to the delivery catheter, as described above in FIG. 14.

Further, the delivery catheter 52 may include a torque shaft 67. The torque shaft 67, preferably formed from hypotubing (e.g., stainless steel or superelastic NiTi) and having an inner lumen 68, is rotatable and disposed within an inner lumen 69 of the inner shaft 62 of the delivery catheter 52. The torque shaft 67 may be secured at a proximal end 70 of the delivery catheter 52 within an adapter 71 with a rotating knob 72. In some such embodiments, an inflation port 73, proximal to the rotating knob 72, is in fluid communication with the inner lumen 68 of the torque shaft 67. A coupling element 74, for example a helical coil screw, is secured to a distal end 75 of the torque shaft 67. Rotation of the torque knob 72 on the proximal end 70 of the torque shaft 67 rotates the coupling element 74 on the distal end 75 of the torque shaft 67 to facilitate deployment of the implantable device 30. An expansion member 76, for example an inflatable balloon, is secured at its proximal end 77 to the torque shaft 67 at a location proximal to the distal end 75 of the torque shaft 67. In some embodiments, the expansion member 76 is secured to the torque shaft 67 by an adhesive or other fastening mechanism in a manner that creates a fluid-tight seal. The expansion member 76 has an interior 79 in fluid communication with the inner lumen 68 of the torque shaft 67. Inflation fluid may be delivered to the interior 79 of the expansion member 76 through the port 73. Inflation of the expansion member 76 by delivering inflation fluid through the port 73 facilitates opening of the implantable device in the ventricle, which in turn facilitates securement of the implantable device 30 to the heart wall.

Figure 12B:
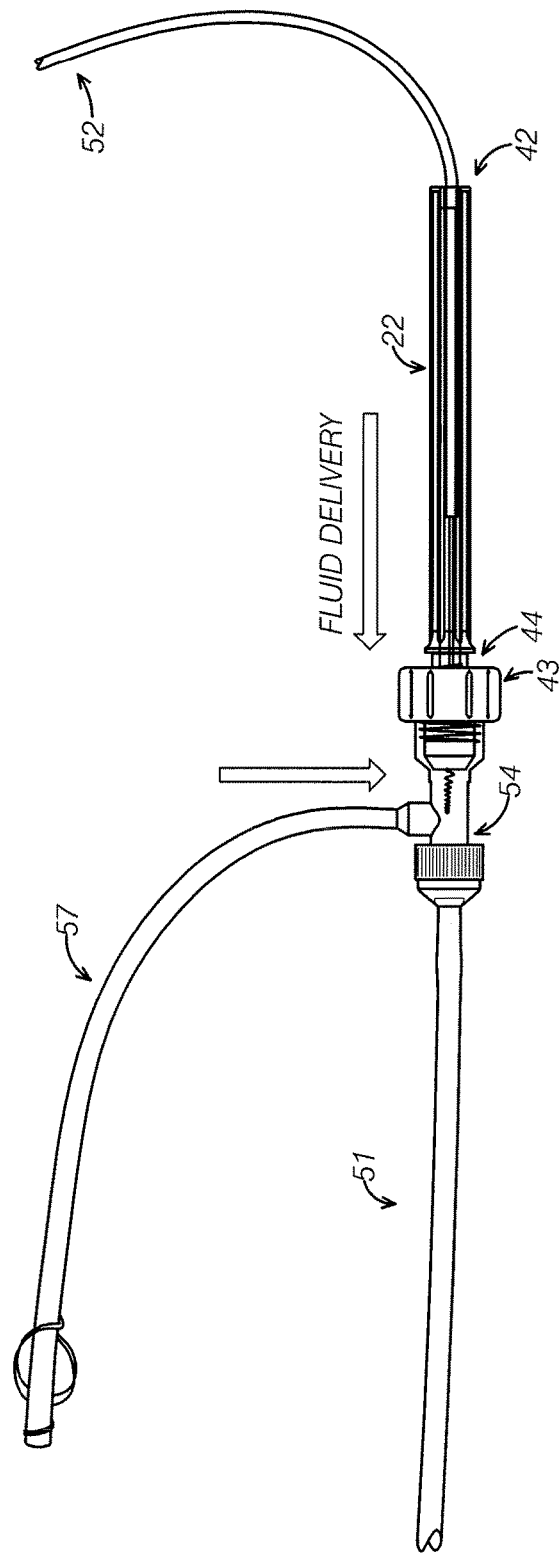
FIG. 12B illustrates one embodiment of a delivery system.
Figure 12C:
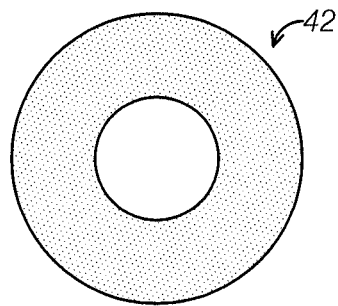
FIGS. 12C-12E illustrate one embodiment of a gasket.
Figure 12D:
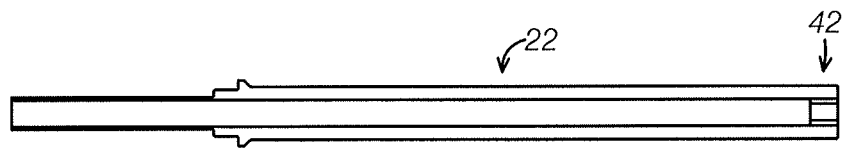
Figure 12E:
Figure 12F:
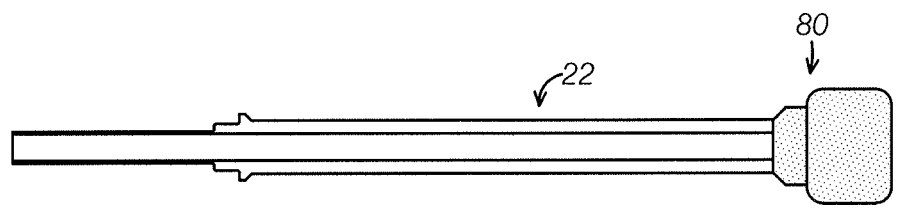
FIG. 12F illustrates one embodiment of a hemostatic valve.
Figure 13:
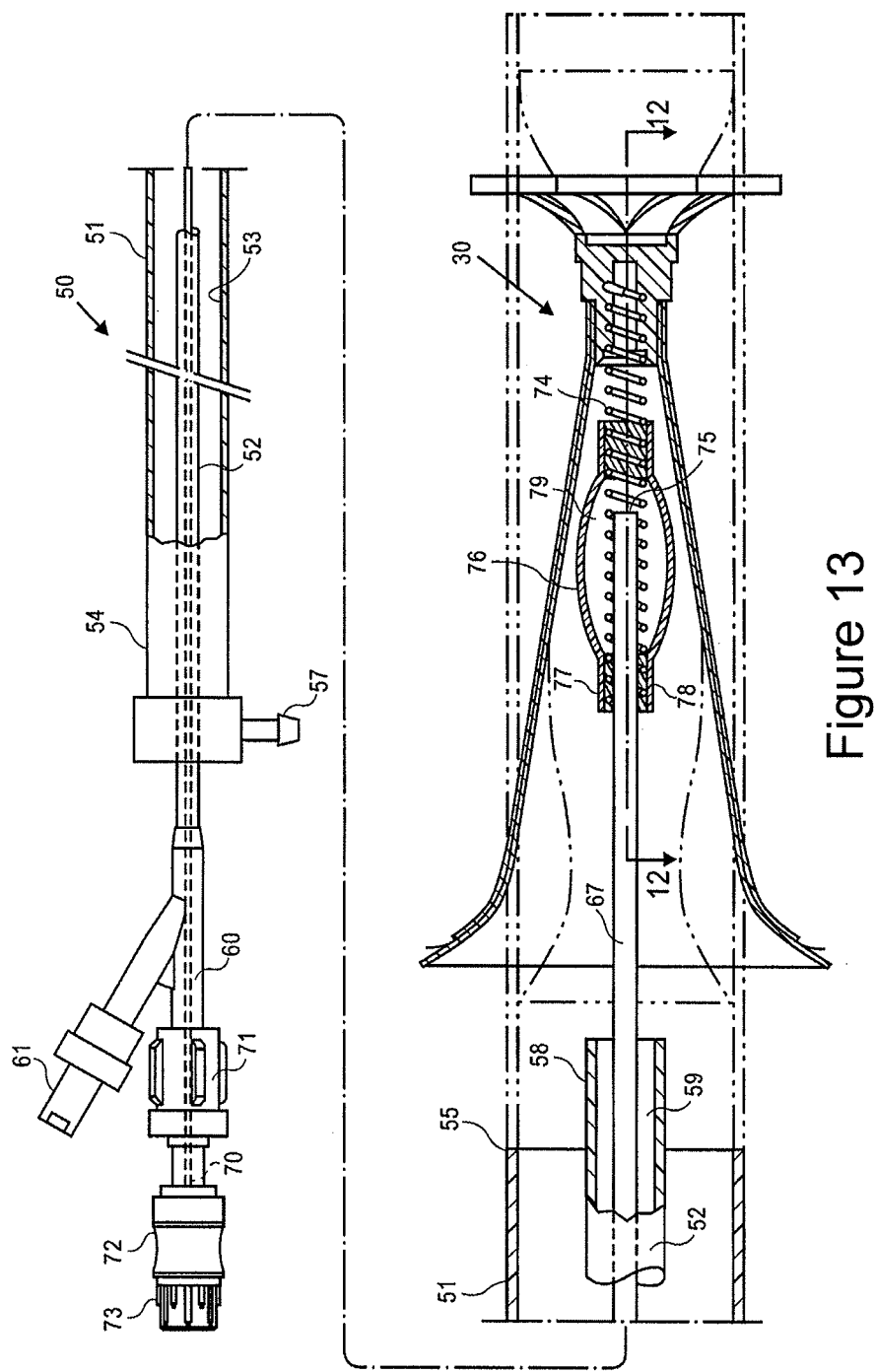
FIG. 13 illustrates one embodiment of a delivery catheter positioned in a guide catheter.

In some embodiments, the mechanical seal 42, as shown in FIGS. 12B-12E, functions to create a liquid-tight or fluid-tight seal between the sleeve 22 and the delivery catheter 52, such that there is reduced loss of liquids from the delivery system. FIG. 12B illustrates the sleeve 22 attached to the guide catheter 51 and the delivery catheter 52 inserted into and through the sleeve 22. FIG. 12C illustrates a front view of an embodiment of the mechanical seal 42 with an opening for removably receiving the delivery catheter 51. FIG. 12D is a cross-sectional view and FIG. 12E is a side view of an embodiment of the sleeve with a mechanical seal 42. The mechanical seal 42 is coupleable to the sleeve 22. In some embodiments, the mechanical seal 42 is sized and positioned to contact an inner surface of the sleeve 22 and an outer surface of the outer shaft 58 of the delivery catheter 52 while the implantable device coupled to the delivery catheter is positioned in the sleeve 22. The mechanical seal may include a gasket, O-ring, bung including an aperture, bodok seal, hermetic seal, diaphragm seal, labyrinth seal, or any other type of seal known to one of skill in the art. The mechanical seal 42 can be located at the proximal end of the sleeve 22. The mechanical seal 42 can be elastic or partially elastic, such as around the opening of the seal, in order to conform to and form a fluid tight seal around the delivery catheter 52.

In some embodiments, as shown in FIGS. 12B-13, the guide catheter 51 functions to receive a ventricular partitioning device from the sleeve 22 and position the ventricular partitioning device in a ventricle. The guide catheter 51 includes a tubular body defining an inner lumen 53 extending between a proximal end 54 and a distal end 55. The proximal end 54 of the guide catheter 51 is coupled to the distal end 44 of the sleeve 22, for example through a connector, a hemostatic valve 43, or any other type of valve. In some embodiments, the guide catheter 51 further includes a second fluid delivery port 57 on the proximal end 54 of the guide catheter 51. The second fluid delivery port 57 is configured for injecting fluids, for example heparinized saline, through the guide catheter. The second fluid delivery port 57 is in fluid communication with the inner lumen 53 of the guide catheter 51.

Methods

Figure 16:
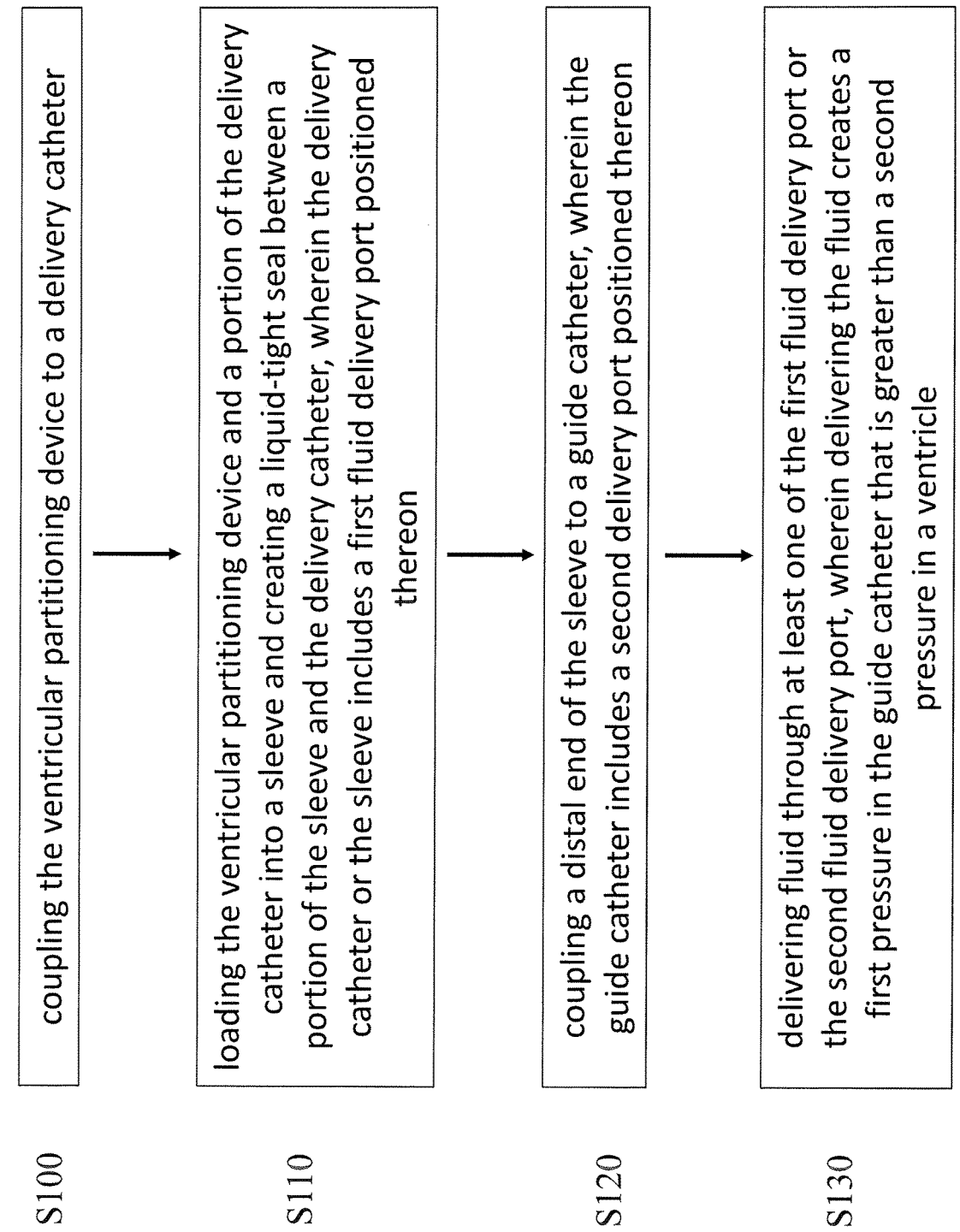
FIG. 16 provides a flow chart depicting one embodiment of a method of preparing a ventricular partitioning device for implantation using a delivery system.

As shown in FIG. 16 a method of preparing a ventricular partitioning device for implantation using a delivery system includes: coupling the ventricular partitioning device to a delivery catheter S100; loading the ventricular partitioning device and a portion of the delivery catheter into a sleeve and creating a liquid-tight seal between a portion of the sleeve and the delivery catheter S110; coupling a distal end of the sleeve to a guide catheter S120; and delivering fluid through a first fluid delivery port disposed on the delivery catheter or the sleeve and/or delivering fluid through a second fluid delivery port disposed on the guide catheter S130. In various embodiments, delivering the fluid creates a first pressure in the guide catheter that is greater than a second pressure in a ventricle. The method of FIG. 16 functions to maintain the ventricular partitioning device relatively free of blood during implantation, reduce or prevent the flow of blood back into the delivery system during implantation of the ventricular partitioning device, reduce friction between the ventricular partitioning device and the delivery system, and facilitate easy opening of the ventricular partitioning device in the ventricle. Alternatively, the methods described may be used in any suitable catheterization and/or implantation procedure or method.

As shown in FIG. 16, one embodiment of preparing a ventricular partitioning device for implantation using a delivery system includes block S100, which recites coupling the ventricular partitioning device to a delivery catheter. S100 functions to attach, screw, adhere, or otherwise fasten the ventricular partitioning device to the delivery catheter. As described above, in one embodiment, the delivery catheter may include a helical screw at the distal tip configured for mating with threads in the stem of the ventricular partitioning device. Alternatively, any other coupling mechanism may be utilized.

As shown in FIG. 16, one embodiment of preparing a ventricular partitioning device for implantation using a delivery system includes block S110, which recites loading the ventricular partitioning device and a portion of the delivery catheter into a sleeve and creating a liquid-tight or fluid-tight seal between a portion of the sleeve and the delivery catheter. In the loaded configuration, the ventricular partitioning device is positioned in the sleeve and the delivery catheter extends out of the first or proximal end of the sleeve. A mechanical seal coupled to the proximal end of the sleeve may create the liquid-tight or fluid-tight seal between the sleeve and the delivery catheter, such that any liquid or fluid injected into the delivery system is substantially maintained in the delivery system. In various embodiments, the delivery catheter or the sleeve includes a first fluid delivery port positioned thereon. S110 functions to prepare a ventricular partitioning device for implantation, for example by collapsing the ventricular partitioning device using the sleeve and positioning the ventricular partitioning device for transfer into a guide catheter. As described above, a funnel may be coupled to the sleeve to facilitate loading of the ventricular partitioning device into the sleeve. In some such embodiments, the ventricular partitioning device coupled to the delivery catheter may be loaded first free ends first into the flared end of the funnel and advanced from the funnel into the sleeve. The funnel may be removed from the sleeve, and as described below, a guide catheter may be coupled in its place at the distal end of the sleeve.

As shown in FIG. 16, one embodiment of preparing a ventricular partitioning device for implantation using a delivery system includes block S120, which recites coupling a distal end of the sleeve to a guide catheter. S120 functions to prepare the ventricular partitioning device for advancement from the sleeve to the guide catheter for delivery into a ventricle. The sleeve of some embodiments is coupled to a valve, such as a hemostatic valve, on the proximal end of the guide catheter. The guide catheter of some embodiments has a second fluid delivery port positioned thereon. In some embodiments, the method includes advancing the ventricular partitioning device coupled to the delivery catheter through one or more valves (e.g., hemostatic valve, check valve, duck-bill valve, etc.) on the proximal end of the guide catheter into the tubular body of the guide catheter.

As shown in FIG. 16, one embodiment of preparing a ventricular partitioning device for implantation using a delivery system includes block S130, which recites delivering fluid through at least one of the first fluid delivery port or the second fluid delivery port, such that delivering the fluid creates a first pressure in the guide catheter that is greater than a second pressure in a ventricle. S130 functions to reduce or prevent blood backflow into the delivery system during implantation of the ventricular partitioning device. Further, flushing the delivery system with saline reduces blood accumulation on the ventricular partitioning device resulting in improved expansion of the ventricular partitioning device upon implantation in the ventricle. In some embodiments, the first pressure is between 200 and 600 mm Hg, and preferably 200-400 mm Hg, and the second pressure is between 0 and 300 mm Hg, and preferably 75-175 mm Hg. The first pressure created in the guide catheter of other embodiments is about 200-250, 250-300, 300-350, 350-400, 400-450, 450-500, 500-550, or 550-600 mm Hg. In one embodiment, the first pressure is about 300 mm Hg. The second pressure in the ventricle of some embodiments is about 5-100, 100-150, 150-200, 200-250, or 250-300 mm Hg. In one embodiment, the second pressure is about 120 mm Hg. In some embodiments, the fluid, for example heparinized saline, is delivered at a positive pressure into the first and/or second fluid delivery ports, such that the pressure in the guide catheter prevents or substantially prevents blood from flowing backwards into the guide catheter, while continued distal movement of the delivery catheter through the guide catheter pushes the ventricular partitioning device out of the guide catheter and into the ventricle. Alternatively, the first and/or second fluid delivery ports may be utilized to remove bubbles from the delivery system, for example, by opening the fluid delivery ports to the atmosphere.

In some embodiments, a method of preparing a ventricular partitioning device for implantation further includes: transferring the ventricular partitioning device from the sleeve to the guide catheter; positioning with a delivery catheter a ventricular partitioning device near an apex of a patient's ventricle; delivering the ventricular partitioning device from the guide catheter into the ventricle; expanding an expansion member coupled to the partitioning device to apply pressure to the plurality of expandable struts to expand the partitioning device; and uncoupling the delivery catheter from the ventricular partitioning device, as described above. In some embodiments, a method of delivering a ventricular partitioning device may further include positioning a delivery sheath over the partitioning device to collapse the partitioning device for removal or redeployment of the partitioning device.

In some embodiments, a method of preparing a ventricular partitioning device for implantation further includes allowing blood from the patient's body to enter the guide catheter through the distal end of the guide catheter and exit the guide catheter through the second fluid delivery port disposed on the guide catheter. This step may occur prior to and/or as the ventricular partitioning device is advanced from the sleeve into the guide catheter. Allowing the backflow of blood into the guide catheter and out the second fluid delivery port removes any air that may be present between the second fluid delivery port and the ventricular partitioning device as the ventricular partitioning device is advanced into the guide catheter.

Further, in some embodiments, delivering fluid through at least one of the first fluid delivery port or the second fluid delivery port includes pushing or otherwise introducing fluid, for example saline, into the guide catheter using the first fluid delivery port disposed on the delivery catheter or the sleeve. In some such embodiments, the fluid is substantially maintained in the guide catheter by the fluid-tight or liquid-tight seal, for example the seal established by the mechanical seal. This fills the space behind the ventricular partitioning device with saline as the ventricular partitioning device is advanced, preventing air from being drawn into the guide catheter.

In some embodiments, a method of preparing a ventricular partitioning device for implantation further includes closing, sealing, or otherwise blocking the second fluid delivery port disposed on the guide catheter after the ventricular partitioning device is advanced distally beyond the second fluid delivery port of the guide catheter. This may ensure, for example, that the saline or other fluid delivered via positive pressure through the first fluid delivery port is not expelled through the second delivery port but rather advances through the guide catheter.

As used in the description and claims, the singular form "a", "an" and "the" include both singular and plural references unless the context clearly dictates otherwise. For example, the term "a fluid delivery port" may include, and is contemplated to include, a plurality of fluid delivery ports. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a device or method consisting essentially of the elements as defined herein would not exclude other materials, features, or steps that do not materially affect the basic and novel characteristic(s) of the claimed invention. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A delivery system for an implantable device, the system comprising:
   a delivery catheter comprising a tubular body having a proximal end and a distal end and an interior lumen, wherein the distal end of the delivery catheter is configured to couple to the implantable device;
   a sleeve defining a lumen configured to receive the delivery catheter and the implantable device coupled thereto;
   a first fluid delivery port positioned on the delivery catheter and in fluid communication with the interior lumen of the delivery catheter;
   a mechanical seal coupled to the sleeve and configured to form a liquid-tight seal with the delivery catheter when the delivery catheter is positioned within the lumen of the sleeve; and
   a guide catheter comprising a tubular body having a proximal end configured for the delivery catheter to be inserted into from the sleeve, a distal end, an interior lumen configured to receive the delivery catheter, and a second fluid delivery port positioned on the guide catheter and in fluid communication with the interior lumen of the guide catheter and configured to be in fluid communication with the interior lumen of the delivery catheter and the first fluid delivery port when the delivery catheter is positioned within the interior lumen of the guide catheter, wherein the proximal end of the guide catheter is configured to be connected to a distal end of the sleeve.

2. The system of claim 1, wherein a first pressure in the guide catheter is greater than a second pressure in a ventricle when fluid is delivered through the guide catheter.

3. The system of claim 1, further comprising a pressurized fluid reservoir configured to be in fluid communication with the delivery catheter.

4. The system of claim 1, further comprising a pump configured to deliver fluid through the delivery catheter.

5. The system of claim 1, wherein the mechanical seal is a gasket.

6. The system of claim 1, wherein the implantable device is a ventricular partitioning device.

7. The system of claim 6, wherein the implantable device comprises a support frame comprising a plurality of radially expandable struts and a membrane coupled to the support frame.

8. The system of claim 7, wherein the implantable device further comprises a foot for contacting a first interior wall portion of a ventricle.

9. The system of claim 1, wherein one or more of the first fluid delivery port or the second fluid delivery port are configured to deliver fluid creating a first pressure in the guide catheter of about 200-600 mm Hg.

10. The system of claim 9, wherein the guide catheter is configured to be positioned in a ventricle having a pressure of about 50-300 mm Hg.

11. The system of claim 1, wherein the guide catheter further comprises a hemostatic valve positioned at the proximal end of the guide catheter.

12. The system of claim 1, wherein one or more of the first fluid delivery port or the second fluid delivery port are configured to deliver fluid creating a positive pressure in the guide catheter.

13. The system of claim 1, further comprising a funnel, wherein the funnel comprises a flared first end and a second end, wherein the flared first end is configured for receiving and collapsing the implantable device, and wherein the second end is coupleable to the sleeve.

14. The system of claim 13, wherein the second end of the funnel is configured to be removed from the distal end of the sleeve prior to the distal end of the sleeve connecting to the proximal end of the guide catheter.

15. The system of claim 1, further comprising a first valve positioned at the proximal end of the guide catheter and configured for the delivery catheter to pass through.

16. The system of claim 15, wherein the first valve is a rotating valve.

17. The system of claim 15, wherein the first valve is configured to connect the proximal end of the guide catheter to the distal end of the sleeve.

18. The system of claim 15, further comprising a second valve positioned at the proximal end of the guide catheter and configured for the delivery catheter to pass through.

19. The system of claim 18, wherein the second valve is configured to reduce fluid backflow before the delivery catheter is inserted into the proximal end of the guide catheter.

20. The system of claim 19, wherein the second valve comprises a check valve.

21. The system of claim 19, wherein the guide catheter includes a T-port, and the first valve, the second valve, and the second fluid delivery port are each positioned on the T-port.

22. The system of claim 1, further comprising a third fluid delivery port positioned on the sleeve and in fluid communication with the lumen of the sleeve.

23. The system of claim 22, wherein the third fluid delivery port is configured to be in fluid communication with the interior lumen of the guide catheter and the second fluid delivery port when the sleeve is connected to the guide catheter.

24. The system of claim 23, wherein the third fluid delivery port is configured to be in fluid communication with the interior lumen of the delivery catheter when the sleeve is connected to the guide catheter and the delivery catheter is positioned within the lumen of the sleeve and the interior lumen of the guide catheter.

25. The system of claim 1, wherein the delivery catheter includes a torque shaft positioned within the interior lumen of the delivery catheter and including a coupling element at a distal end of the torque shaft and configured to couple to the implantable device.

26. The system of claim 25, wherein the delivery catheter includes an expansion member positioned at the distal end of the torque shaft and configured to open the implantable device in a ventricle, wherein the torque shaft includes an inner lumen in fluid communication with the expansion member.

27. The system of claim 26, further comprising an inflation port in fluid communication with the inner lumen of the torque shaft and configured to pass fluid through the inner lumen to inflate the expansion member.

28. The system of claim 27, further comprising a torque knob configured to be rotated to deploy the implantable device from the coupling element.

29. The system of claim 25, wherein the delivery catheter includes an outer shaft defining the interior lumen of the delivery catheter, and the torque shaft is configured to extend distally from an opening of the outer shaft.

30. The system of claim 29, wherein the opening of the outer shaft is configured to be positioned proximal of the coupling element and in fluid communication with the interior lumen of the guide catheter and the second fluid delivery port when the outer shaft is positioned within the interior lumen of the guide catheter.

31. The system of claim 1, wherein the first fluid delivery port is configured to introduce fluid into the interior lumen of the guide catheter when the delivery catheter is positioned within the interior lumen of the guise catheter.

* * * * *